(12) United States Patent
Delvalle et al.

(10) Patent No.: US 9,492,369 B2
(45) Date of Patent: Nov. 15, 2016

(54) EMULSIONS CONTAINING SACCHARIDE SILOXANE COPOLYMER EMULSIFIERS AND METHODS FOR THEIR PREPARATION AND USE

(75) Inventors: Cindy Delvalle, Uccle (BE); Eric Jude Joffre, Midland, MI (US); Concettina Scavuzzo, Chap.-lez-Herlaimont (BE); Simon Toth, Midland, MI (US); Isabelle Van Reeth, Shanghai (CN)

(73) Assignee: Dow Corning Corporation, Midland, MI (US)

( * ) Notice: Subject to any disclaimer, the term of this patent is extended or adjusted under 35 U.S.C. 154(b) by 553 days.

(21) Appl. No.: 13/817,660

(22) PCT Filed: Aug. 15, 2011

(86) PCT No.: PCT/US2011/047718
§ 371 (c)(1),
(2), (4) Date: Feb. 19, 2013

(87) PCT Pub. No.: WO2012/027144
PCT Pub. Date: Mar. 1, 2012

(65) Prior Publication Data
US 2013/0149260 A1 Jun. 13, 2013

Related U.S. Application Data

(60) Provisional application No. 61/375,938, filed on Aug. 23, 2010, provisional application No. 61/407,981, filed on Oct. 29, 2010.

(51) Int. Cl.
| | |
|---|---|
| C08G 77/26 | (2006.01) |
| A61K 8/73 | (2006.01) |
| A61K 8/06 | (2006.01) |
| A61K 8/898 | (2006.01) |
| A61Q 19/00 | (2006.01) |
| C08G 77/388 | (2006.01) |
| C08G 77/42 | (2006.01) |
| A61Q 1/02 | (2006.01) |
| A61Q 1/06 | (2006.01) |
| A61Q 1/10 | (2006.01) |
| A61Q 3/00 | (2006.01) |
| A61Q 5/02 | (2006.01) |
| A61Q 5/06 | (2006.01) |
| A61Q 5/12 | (2006.01) |
| A61Q 9/00 | (2006.01) |
| A61Q 11/00 | (2006.01) |
| A61Q 13/00 | (2006.01) |
| A61Q 15/00 | (2006.01) |
| A61Q 17/04 | (2006.01) |
| C08G 77/16 | (2006.01) |

(52) U.S. Cl.
CPC . *A61K 8/73* (2013.01); *A61K 8/06* (2013.01); *A61K 8/898* (2013.01); *A61Q 1/02* (2013.01); *A61Q 1/06* (2013.01); *A61Q 1/10* (2013.01); *A61Q 3/00* (2013.01); *A61Q 5/02* (2013.01); *A61Q 5/06* (2013.01); *A61Q 5/065* (2013.01); *A61Q 5/12* (2013.01); *A61Q 9/00* (2013.01); *A61Q 11/00* (2013.01); *A61Q 13/00* (2013.01); *A61Q 15/00* (2013.01); *A61Q 17/04* (2013.01); *A61Q 19/00* (2013.01); *C08G 77/388* (2013.01); *C08G 77/42* (2013.01); *A61K 2800/10* (2013.01); *C08G 77/16* (2013.01); *C08G 77/26* (2013.01)

(58) Field of Classification Search
CPC ...... C08G 77/16; C08G 77/26; C08G 77/42; C08G 77/388
See application file for complete search history.

(56) References Cited

U.S. PATENT DOCUMENTS

| | | | |
|---|---|---|---|
| 5,004,791 A | 4/1991 | Billmers | |
| 5,100,991 A * | 3/1992 | Cray et al. | 528/26 |
| 5,831,080 A * | 11/1998 | Sejpka et al. | 536/124 |
| 5,891,977 A | 4/1999 | Dietz et al. | |
| 6,066,727 A | 5/2000 | Yamamoto et al. | |
| 6,255,429 B1 | 7/2001 | Griffin et al. | |
| 6,471,952 B1 | 10/2002 | Dubief et al. | |
| 6,762,289 B1 | 7/2004 | O'Lenick, Jr. et al. | |
| 2004/0186308 A1* | 9/2004 | Koch et al. | 556/413 |
| 2008/0138386 A1 | 6/2008 | Joffre et al. | |
| 2008/0199417 A1* | 8/2008 | Joffre et al. | 424/70.12 |
| 2008/0200612 A1 | 8/2008 | Joffre et al. | |
| 2008/0209645 A1 | 9/2008 | Carrillo et al. | |
| 2009/0258058 A1 | 10/2009 | Thomas et al. | |
| 2011/0065863 A1* | 3/2011 | Fitremann et al. | 525/54.2 |

FOREIGN PATENT DOCUMENTS

| | | |
|---|---|---|
| JP | 62068820 | 3/1987 |
| WO | 9429324 | 12/1994 |
| WO | WO 01/87063 A2 | 11/2001 |
| WO | 02088456 | 11/2002 |
| WO | 2006127924 | 11/2006 |
| WO | WO 2006/127882 A2 | 11/2006 |
| WO | 2008103219 | 8/2008 |
| WO | 2009125126 | 10/2009 |

* cited by examiner

*Primary Examiner* — Margaret Moore
(74) *Attorney, Agent, or Firm* — Catherine U. Brown

(57) ABSTRACT

An emulsion contains a saccharide siloxane copolymer as an emulsifier. The emulsion is useful in formulating personal care products.

32 Claims, No Drawings

EMULSIONS CONTAINING SACCHARIDE SILOXANE COPOLYMER EMULSIFIERS AND METHODS FOR THEIR PREPARATION AND USE

CROSS REFERENCE TO RELATED APPLICATIONS

This application is a U.S. national stage filing under 35 U.S.C. §371 of PCT Application No. PCT/US11/47718 filed on Aug. 15, 2011, currently pending, which claims the benefit of U.S. Provisional Patent Application No. 61/375,938 filed Aug. 23, 2010 and U.S. Provisional Patent Application No. 61/407,981 filed Oct. 29, 2010 under 35 U.S.C. §119 (e). PCT Application No. PCT/US11/47718 and U.S. Provisional Patent Application No. 61/375,938 and U.S. Provisional Patent Application No. 61/407,981 are hereby incorporated by reference.

BACKGROUND OF THE INVENTION

Saccharide siloxanes are known in the art. Saccharide siloxanes comprising a hydroxyl functional saccharide component and an organosiloxane component were found to be useful when applied to hair, skin, fabric, paper, wood and other substrates. The saccharide component may be covalently bound to the organosiloxane at one or more pendant or terminal positions, or some combination thereof, through linkages including but not limited to ether, ester, and amide bonds.

BRIEF SUMMARY OF THE INVENTION

A saccharide siloxane copolymer (copolymer) is useful as an emulsifier. Emulsions containing the copolymer are useful for personal care applications.

DETAILED DESCRIPTION OF THE INVENTION

A saccharide siloxane copolymer (copolymer) is useful as an emulsifier, for water in oil (w/o) type emulsions, such as water in silicone emulsions. The copolymer comprises a saccharide component and a siloxane component. The siloxane component forms the backbone of the copolymer molecule. Saccharide components may be bonded to the siloxane backbone in terminal groups, pendant groups, or both terminal and pendant groups. Alternatively, the saccharide component may be bonded to the siloxane backbone in a pendant group.

The copolymer may be a solid or a fluid under ambient conditions of temperature and pressure, e.g., at 25° C. and 760 mmHg. Whether the copolymer is a solid at ambient conditions, or a fluid such as a liquid or a gum, depends on various factors including the degree of polymerization (DP) of the copolymer. The copolymer may have a DP ranging from 2 to 15,000, alternatively 5 to 10,000, alternatively 50 to 5,000, alternatively, 100 to 1,000, alternatively 50 to 1,000, and alternatively 100 to 400.

Alternatively, the copolymer may be a fluid under ambient conditions of temperature and pressure, e.g., at 25° C. and 760 mmHg. The viscosity of the copolymer depends on various factors including the degree of polymerization (DP) of the copolymer. The copolymer may have a DP ranging from 2 to 500, alternatively 5 to 500, alternatively, 25 to 500, alternatively 50 to 400, alternatively 100 to 400, and alternatively 50 to 350.

The copolymer has general formula:

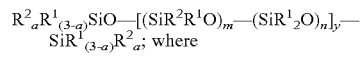

$R^2{}_a R^1{}_{(3-a)} SiO—[(SiR^2R^1O)_m—(SiR^1{}_2O)_n]_y—SiR^1{}_{(3-a)}R^2{}_a$; where each $R^1$ can be the same or different and each $R^1$ comprises hydrogen, an alkyl group of 1 to 12 carbon atoms, an organic group, or a group of formula $R^3$-Q;

Q comprises an epoxy, cycloalkylepoxy, primary or secondary amino, ethylenediamine, carboxy, halogen, vinyl, allyl, anhydride, or mercapto functionality;

subscripts m and n are integers from 0 to 15,000 and may be the same or different; each subscript a is independently 0, 1, 2, or 3;

subscript y is an integer such that the copolymer has a molecular weight less than 1 million;

each $R^2$ has formula $Z-(G^1)_b-(G^2)_c$, and there is an average of at least one $R^2$ per copolymer molecule, where $G^1$ is a saccharide component comprising 5 to 12 carbon atoms, a quantity (b+c) has a value ranging from 1 to 10, and subscript b or subscript c can be 0, $G^2$ is a saccharide component comprising 5 to 12 carbon atoms additionally substituted with organic or organosilicon radicals, each Z is a linking group and is independently selected from the group consisting of: —$R^3$—N($R^8$)—C(O)—$R^4$—, —$R^3$—CH(OH)—CH$_2$—N($R^8$)—$R^4$—, or $R^3$—CH(N($R^4$)($R^8$))CH$_2$OH;

where each $R^3$ and each $R^4$ are divalent spacer groups comprising a group of formula $(R^5)_r(R^6)_s(R^7)_t$, where at least one of subscripts r, s and t is 1, and each $R^5$ and each $R^7$ are independently either an alkylene group of 1 to 12 carbon atoms or a group of formula $(R^9O)_p$, where subscript p is an integer with a value ranging from 1 to 50, and each $R^9$ is a divalent organic group, and each $R^9O$ may be the same or different, each $R^6$ is —N($R^8$)—, where $R^8$ is selected from $R^3$, a monovalent hydrocarbon group, a group of formula Z—X, or a reaction product of —N(H)— with an epoxy functional group, a cycloalkylepoxy functional group, a glycidyl ether functional group, an acidic anhydride functional group, or a lactone;

each X is independently a divalent carboxylic acid, phosphate, sulfate, sulfonate or quaternary ammonium radical, and with the provisos that at least one of $R^3$ and $R^4$ must be present in the linking group, and each $R^3$ and each $R^4$ may be the same or different.

Each $R^1$ can be the same or different. Each $R^1$ comprises hydrogen, an alkyl group of 1 to 12 carbon atoms, an organic group, or a group of formula $R^3$-Q. Group Q comprises an epoxy, cycloalkylepoxy, primary or secondary amino, ethylenediamine, carboxy, halogen, vinyl, allyl, anhydride, or mercapto functionality.

Subscripts m and n are integers from 0 to 15,000 and may be the same or different. Alternatively, each subscript m may be 0 to 500 and each subscript n may be 0 to 500. Each subscript a is independently 0, 1, 2, or 3. Alternatively, each subscript a may be 0. When subscript a is 0, then at least one of subscripts m and n is greater than 0, and all of the saccharide components are in pendant groups (not terminal groups) on the copolymer. Subscript y is an integer such that the copolymer has a molecular weight less than 1 million.

Subscript y, and at least one of subscripts m and n, may be greater than 0 such that a saccharide component is in a pendant group on the copolymer.

Each $R^2$ has formula $Z\text{-}(G^1)_b\text{-}(G^2)_c$, and there is an average of at least one $R^2$ per copolymer molecule. Group $G^1$ is a saccharide component comprising 5 to 12 carbon atoms. Subscript b or subscript c can be 0. However, a quantity (b+c) has a value ranging from 1 to 10. Group $G^2$ is a saccharide component comprising 5 to 12 carbon atoms additionally substituted with organic or organosilicon groups. Substituted means that a hydrogen atom bonded to a carbon atom has been replaced with another substituent, such as with an organic group or an organosilicon group. Each Z is a linking group.

Each Z is independently selected from the group consisting of: $-R^3-N(R^8)-C(O)-R^4-$, $-R^3-CH(OH)-CH_2-N(R^8)-R^4-$, or $-R^3-CH(N(R^4)(R^8))CH_2OH$. Each $R^3$ and each $R^4$ are divalent spacer groups comprising a group of formula $(R^5)_r(R^6)_s(R^7)_t$. At least one of subscripts r, s and t is 1. Each $R^5$ and each $R^7$ are independently either an alkylene group of 1 to 12 carbon atoms or a group of formula $(R^9O)_p$. Subscript p is an integer with a value ranging from 1 to 50. Each $R^9$ is a divalent organic group. Each $R^9O$ may be the same or different. Alternatively, each $R^5$ and each $R^7$ are independently an alkylene group of 1 to 12 carbon atoms, and the copolymer may be free of groups of formula $R^9O$. Without wishing to be bound by theory, it is thought that copolymers free of groups of formula $R^9O$ when used as emulsifiers may provide low odor emulsions. Each $R^6$ is $-N(R^8)-$, where $R^8$ is selected from $R^3$, a group of formula Z—X, a monovalent hydrocarbon group, or a reaction product of —N(H)— with an epoxy functional group, a cycloalkylepoxy functional group, a glycidyl ether functional group, an acetic anhydride functional group, or a lactone. Suitable monovalent hydrocarbon groups for $R^8$ may be a saturated hydrocarbon group or an unsaturated hydrocarbon group. When $R^8$ is an unsaturated hydrocarbon group, $R^8$ may be an alkenyl group. The alkenyl group may have 2 to 12 carbon atoms and is exemplified by vinyl, allyl, decenyl, and dodecenyl. Alternatively, the alkenyl group may have a longer chain such as at least 14 carbon atoms. When $R^8$ is a saturated hydrocarbon group, $R^8$ may be an alkyl group. The alkyl group may be relatively short chain, such as 1 to 12 carbon atoms. Alternatively, the alkyl group may have a longer chain, such as at least 14 carbon atoms. Each X is independently a divalent a carboxylic acid, phosphate, sulfate, sulfonate or quaternary ammonium radical. At least one of $R^3$ and $R^4$ must be present in the linking group. Each $R^3$ and each $R^4$ may be the same or different.

Method of Making the Copolymer

The copolymer described above may be made by a method comprising: 1) reacting an organofunctional polyorganosiloxane with a sugar moiety to produce a saccharide siloxane copolymer as described above and 2) removing all or a portion of a solvent, if a solvent is present.

In one embodiment, the method for making the copolymer comprises:
1) reacting an amine functional polyorganosiloxane containing a primary amine and a secondary amine with a sugar lactone to consume the primary amine,
2) reacting the product of step 1) with a capping agent to block the secondary amine.

Steps 1) and 2) may be performed sequentially. Alternatively, step 1 and step 2 may be combined and performed simultaneously.

The secondary amine functionality may be selected from aminopropyl, aminoethylaminopropyl, and aminoethylaminoisobutyl. The sugar lactone may be an aldonolactone or another lactone derived from a saccharide. Aldonolactones are lactones derived from aldonic acids. The capping agent may be a lactone, a halogenated unsaturated compound, an epoxy functional compound, or an acid anhydride.

Step 1) may be performed by reacting (A) an aminofunctional polyorganosiloxane and (B) an aldonolactone. Ingredient (A) may have the formula:

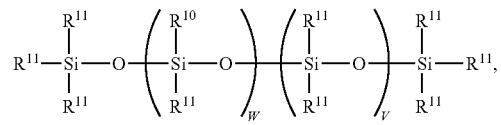

where
each $R^{10}$ is a independently secondary amino group; each $R^{11}$ is independently a monovalent hydrocarbon group or $R^{10}$; subscript w has a value ranging from 0 to 10,000, and subscript v has a value ranging from 0 to 10,000, with the proviso that when all instances of $R^{11}$ are monovalent hydrocarbon groups, then subscript w is greater than 0. The secondary amino group may be, for example, aminoethylaminoisobutyl or aminoethylaminopropyl.

Ingredient (A) is exemplified by trimethylsiloxy-terminated poly(dimethylsiloxane/methyl(aminoethylaminoisobutyl)siloxane); trimethylsiloxy-terminated poly(dimethylsiloxane/methyl(aminoethylaminopropyl)siloxane); dimethyl, methyl(aminoethylaminoisobutyl)siloxy-terminated, polydimethylsiloxane; dimethyl, methyl(aminoethylaminopropyl)siloxy-terminated, polydimethylsiloxane; and combinations thereof.

Ingredient (B) is an aldonolactone or another lactone derived from a saccharide. The aldonolactone suitable for ingredient (B) is exemplified by gluconolactone (GL), erythronolactone, galactonolactone, gluconolactone, mannonolactone, and ribolactone. Other lactones derived from saccharides can include glucoronolactone, glucoheptanolactone, glucooctanolactone, isocitric acid lactone, saccharolactone, and lactobionolactone (LBL). Alternatively, ingredient (B) may be GL or LBL. Lactones suitable for ingredient (B) are commercially available.

Step 2) may be performed by reacting the product of step 1) with (C) a capping agent to block the secondary amine. The capping agent may be a lactone, a halogenated unsaturated compound capable of reacting with the hydrogen on the secondary amine functionality, an epoxy functional compound, or an acid anhydride.

The capping agent may be a lactone. The lactone may have the formula:

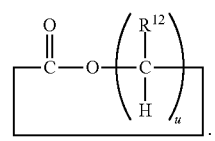

Each $R^{12}$ is independently a hydrogen atom, a hydroxyl group, an alkoxy group, or a saccharide group. Alkoxy groups are exemplified by methoxy, ethoxy, propoxy, and butoxy. Alternatively, each $R^{12}$ is a hydroxyl group or a saccharide group. Subscript u has a value ranging from 5 to 12. The lactone used in step 2) may be exemplified by the sugar lactones described above. Alternatively, the lactone may be butyrolactone, epsilon caprolactone, gamma gluconolactone, delta gluconolactone, and LBL. Alternatively, the lactone may be gamma gluconolactone or delta gluconolactone.

Alternatively, the capping agent may be halogenated unsaturated compound capable of reacting with the hydrogen atom on the secondary amine. The halogenated unsaturated compound may be a halogenated unsaturated hydrocarbon such as an alkenyl chloride. Suitable alkenyl chlorides may have 2 to 12 carbon atoms and may include vinyl chloride, allyl chloride, decyl chloride, or dodecyl chloride.

Alternatively, the capping agent may be an epoxy functional compound. The epoxy functional compound may be selected from allyl epoxy functional compounds, cycloalkylepoxy functional compounds, glycidyl ether functional compounds, and glycidol.

Alternatively, the capping agent may be an acidic anhydride. The acid anhydride may have the formula:

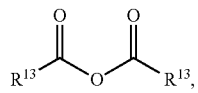

where each $R^{13}$ is independently a monovalent hydrocarbon group. Alternatively, each $R^{13}$ may be an alkyl group, such as an alkyl group of 1 to 12 carbon atoms. Suitable alkyl groups are represented by methyl, ethyl, propyl, and butyl. Alternatively, the acid anhydride may comprise acetic anhydride, chloroacetic anhydride, propionic anhydride, crotonic anhydride, methacrylic anhydride, butyric anhydride, isobutyric anhydride, diethyl pyrocarbonate, or 4-pentenoic anhydride. Alternatively, the acid anhydride may be acetic anhydride.

Alternatively, the copolymer may be prepared by a method comprising reacting an epoxy functional polyorganosiloxane with an n-alkyl glucamine such as n-methyl glucamine. The epoxy functional polyorganosiloxane may be prepared by methods known in the art, such as by hydrosilylation of ingredients comprising an alkenyl functional epoxy containing compound and a polyorganohydrogensiloxane. The alkenyl functional epoxy containing compound may be allyl glycidyl ether, dodecenyl glycidyl ether, tetradecenyl glycidyl ether, or octadecenylglycidyl ether. The ingredients may optionally further comprise further comprise an alkene, such as undecene. Alternatively, one skilled in the art could react the n-alkyl-glucamine first with the alkenyl functional epoxy containing compound and thereafter perform the hydrosilylation reaction to attach the product thereof to the polyorganohydrogensiloxane.

Alternatively, the copolymer may be prepared by a method comprising:
1) reacting an n-alkyl-glucamine with an alkenyl functional epoxy compound, and
2) hydrosilylating the product of step 1) with a polyorganohydrogensiloxane.

Steps 1) and 2) may be performed sequentially. Alternatively, step 1 and step 2 may be combined and performed simultaneously.

In this method, the alkenyl functional epoxy containing compound may be allyl glycidyl ether, dodecyl glycidyl ether, tetradecyl glycidyl ether, or octadecylglycidyl ether. The n-alkyl glucamine may be n-methyl glucamine.

The methods described above may be performed neat or in the presence of a solvent. The solvent may be an alcohol such as methanol, ethanol, propanol, butanol, or a combination thereof. Alternatively, the organo-functional polyorganosiloxane (e.g., amine functional polyorganosiloxane, or epoxy functional polyorganosiloxane, or the polyorganohydrogensiloxane) may be dissolved in a solvent such as ethanol with the other ingredients used in the method. All or a portion of the solvent may be removed, for example, by stripping or distillation, after the method is complete. Alternatively, the copolymer may be left in the solvent after the method is complete, for example, if the solvent is a suitable ingredient for an emulsion in which the copolymer will be formulated.

Alternatively, the methods described above may be performed in the presence of an oil. The oil may be added in addition to the solvent. The oil may be added before reacting the ingredients to make the copolymer. Alternatively, the oil may be added during and/or after making the copolymer and before removal of any solvent. Alternatively, the oil may be added after a portion of the solvent is removed. Alternatively, the oil may be added after all of the solvent is removed.

The methods described above may be performed by heating. The exact temperature depends on various factors including the specific ingredients selected, however, temperature may range from 50° C. to 100° C. and reaction time for each step may be several hours, alternatively, up to 10 hours, alternatively 1 to 10 hours. The first and second steps in the methods described above may be performed sequentially. Alternatively, step 1 and step 2 may be combined and performed simultaneously.

In the methods described above a molar excess may be used of the functionality on the reagent reacting with the functionality on the polyorganosiloxane. For example, in the hydrosilylation of allyl glycidyl ether with an SiH intermediate polyorganosiloxane, a 1.1:1 ratio is used of the moles allyl glycidyl ether to the moles of SiH. The ratio for the reagent to siloxane bonded functionality may be as large as 1.8:1. Alternatively, the molar ratio may range from 1:1 to 1.8:1, alternatively 1.1:1 to 1.5:1.

Alternatively, the molar ratio of sugar lactone to amine may be 1:1, calculated from amine value of the amine functional polyorganosiloxanes. However, the molar ratio of sugar functionality in the sugar lactone to amine in the amine functional polyorganosiloxane may range from 0.5:1 to 2.0:1.

DEFINITIONS AND USAGE OF TERMS

All amounts, ratios, and percentages are by weight unless otherwise indicated. As used herein, the articles 'a' 'an' and 'the' each refer to one or more, unless otherwise indicated by the context of the application.

The art of "personal care" is intended to include any topical treatment of any portion of the body that is intended to provide a benefit to that portion of the body. The a benefit may be direct or indirect, and may be sensory, mechanical, cosmetic, protective, preventative or therapeutic. While it is contemplated that the human body is a particularly desirable target substrate for the presently disclosed personal care compositions and products formulated therefrom, it will be readily apparent to one skilled in the art that other mammals having similar tissues, especially keratinacious tissue such as skin and hair, may be suitable target substrates and that therefore veterinary applications are within the scope of the present invention.

The personal care compositions, as provided, are adapted to provide a benefit to a portion of the body. As used herein, "adapted" means formulated in a manner that permits safe and effective application of the benefit to the portion of the body. As used herein, "safe and effective" means an amount that provides a level of benefit perceivable by a consumer seeking such a benefit without damaging or causing significant discomfort to the consumer seeking such a benefit. A significant discomfort is one that outweighs the benefit provided such that an ordinary consumer will not tolerate it.

A person of ordinary skill in the personal care formulation arts will appreciate the well-known criterion for selecting the essential ingredients, optional additives and excipients, that are suitable according to the intended application of a particular personal care composition. Non-limiting examples of additives which may be formulated into the personal care compositions with the emulsion include: additional silicones, aerosols, anti-oxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sunscreening agents, suspending agents, tanning agents, other surfactants, thickeners, vitamins, botanicals, waxes, rheology-modifying agents, anti-dandruff, anti-acne, anti-carie and wound healing-promotion agents.

The term "emulsion" as used herein means a two phase system comprising two immiscible liquids with the liquid constituting the first, dispersed internal (discontinuous) phase being suspended in the second, continuous phase with the aid of the copolymer described above as an emulsifier.

Emulsions

The copolymer described above was surprisingly found to have improved emulsification properties as compared to some previously known saccharide siloxanes. Therefore, an emulsion including the copolymer as an emulsifier may be prepared. The emulsion may be a water in oil (w/o) emulsion comprising an internal, aqueous phase comprising water and an external, continuous phase comprising an oil and the copolymer as the emulsifier. Without wishing to be bound by theory, it is thought that the emulsion need not further comprise any surfactant other than the copolymer to maintain the dispersion of the internal phase.

The oil used in the continuous phase of the emulsion may be a silicone oil or an organic oil. The oil may be a silicone oil such as a polydialkylsiloxane having a viscosity of 1 to 350 cSt. Such silicone oils are commercially available as DOW CORNING® 200 Fluids with viscosities ranging from 2 centiStokes (cSt) to 350 cSt, and DOW CORNING® FZ-3196, DOW CORNING® 244 Fluid, and DOW CORNING® 245 Fluid from Dow Corning Corporation of Midland, Mich., U.S.A. Dimethicone oils from Dow Corning Corporation include 244 Fluid, 245 Fluid, and 200 Fluids with viscosity of 2 cSt, 5 cSt, 10 cSt 20 cSt, 50 cSt, 100 cSt, or 350 cSt.

Alternatively, certain organic oils are suitable for use in the emulsion. Suitable organic oils include esters, vegetable and/or mineral oils, hydrocarbon oils, or fatty alcohols.

Suitable esters include isopropyl myristate, octyl octanonanoate, decyl oleate, isopropyl palmitate, glyceryl stearate, ethylhexyl stearate, isopropyl isostearate, C12-C15 alkyl benzoate, octyl cocoate, octyl palmitate, myristyl lactate, and dioctyl adipate. Examples of esters further comprise cetyl ethylhexanoate (which is commercially available as Schercemol™ Colo. Ester from The Lubrizol Corporation of Wickliffe, Ohio, U.S.A.) and triethylhexanoin (which is commercially available as Schercemol™ GTO Ester, also from Lubrizol).

Suitable vegetable and mineral oils include almond oil, apricot kernel, avocado oil, castor oil, evening primrose, jojoba oil, sunflower oil, olive oil, wheat germ oil, and mineral oil.

Suitable hydrocarbon oils include petrolatum, mineral oil, squalene, capric/caprylic triglyceride; an alkane of at least 12 carbon atoms. For example, long chain alkanes (e.g., alkanes having at least 12 carbon atoms, such as isododecane or isohexadecane) may be used as the organic oil.

Suitable fatty alcohols that include strearyl alcohol, cetyl alcohol.

The emulsion may be prepared by a method comprising dispersing the copolymer described above in an oil and thereafter adding the aqueous phase. The aqueous phase may be added to the oil phase in increments with mixing between additions. The resulting combination of aqueous and oil phases may be subjected to high shear. The oil forms the external or continuous phase. Mixing may be performed, for example, by mixing with a cross stirrer at 700 to 1,000 revolutions per minute (rpm) while adding the aqueous phase. After the aqueous phase has been added, the resulting mixture may optionally be further mixed at 1,000 to 2,000 rpm for a period of time such as 1 second to 10 minutes, alternatively 1 minute to 5 minutes. For example, mixing conditions after all the aqueous phase have been added may include mixing for 1 minute at 1,000 rpm and then 5 minutes at 2,000 rpm. A low shear mixer, such as a planetary type mixer may be used for this method step. Without wishing to be bound by theory, it is thought that the emulsion may be a coarse emulsion that may have a relatively large particle size (e.g., on the order of 5 micrometers or higher) using low shear mixing.

The high shear mixing may be performed using special equipment, which allows to the emulsion mix at very high shear to reduce particle size and increase the viscosity of the emulsion. High shear mixing may improve stability of the emulsion. The high shear mixing may be performed with a commercially available high shear device, e.g., a homogenizer such as a T25 Digital ULTRA-TURRAX® commercially available from IKA of Wilmington, N.C., U.S.A. or a homogenizer such as L4RT commercially available from Silverson Machines Ltd. of England. The exact conditions for high shear mixing will vary depending on factors such as the initial viscosity of the emulsion, however, high shear conditions are exemplified by mixing the emulsion at 7,000 to 8,000 rpm for 1 second to 1 minute, alternatively 15 seconds. Without wishing to be bound by theory, it is thought that the emulsion may be a fine emulsion that may have a relatively small particle size (e.g., on the order of less than 5 micrometers) after high shear mixing.

It will be understood by one of ordinary skill in the art that there is a continuum for the ease with which a desired emulsion forms. The emulsions described herein share similar constraints with other emulsions. That is, they are thermodynamically unstable and need an input of energy to initiate emulsification. Simple agitation via mixing may be sufficient, or higher shear means including the employment of high shear devices may be used. Alternatively, an inversion method may be used.

A degree of agitation necessary to form the emulsion may require employment of mixing devices. Mixing devices typically provide the required energy input. Non-limiting examples of these mixing devices spanning the shear range include: 1) a vessel with an impeller, for example, propeller, pitched blade impeller, straight blade impeller, Rushton impeller, or Cowles blade; 2) kneading type mixers, for example, Baker-Perkins; 3) high shear devices which use positive displacement through an orifice to generate shear, for example, homogenizer, sonolator, or microfluidizer; 4) high shear devices using a rotor and stator configuration, for example, colloid mills, homomic line mills, homogenizers from IKA, or Bematek; 5) continuous compounders with single or dual screws; 6) change can mixers with internal impellers or rotor/stator devices, for example, Turello mixer; and 7) centrifugal mixers, for example, Hauschild speedmixers. Combinations of mixing devices can also provide benefits, for example a vessel with an impeller can be connected to a high shear device. High shear devices are known in the art and are commercially available, for example, the high shear device may be a homogenizer such as a T25 Digital ULTRA-TURRAX® commercially available from IKA of Wilmington, N.C., U.S.A. or high shear mixer from Silverson Machines Ltd. of England.

The choice of mixing device is based on the type of internal phase to be emulsified. For example, low viscosity internal phases can be emulsified using high shear devices which use positive displacement through an orifice. However, in the case of high viscosity internal phases, a rotor/stator device, twin screw compounder or change can mixer are often better choices.

The order of ingredient addition in the preparation of the emulsion may be determined empirically. For example, a desirable order of addition for a thick-phase emulsification may be: (a) combine the copolymer with an oil; (b) add aqueous phase comprising water in increments with shear until a thick phase emulsion forms; and optionally (c) further dilute with additional oil and/or oil phase to a desired concentration, with shear. The method may optionally further comprise adding an additional ingredient, such as those described below.

Emulsions made with the copolymer may be useful in personal care products. Therefore, the method may optionally further comprise formulating a personal care product with the emulsion. The personal care products may be functional with respect to the portion of the body to which they are applied, cosmetic, therapeutic, or some combination thereof. Conventional examples of such products include, but are not limited to: antiperspirants and deodorants, skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, wrinkle fillers, skin imperfection hiders, skin surface smoothers, eyelash curlers, nail varnishes, hair make-up products, eye shadows, body makeups, and powders, medicament creams, pastes or sprays including anti-acne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

In some personal care product embodiments comprising the emulsion, inclusion of the copolymer may decrease the need for other thickening agents in the formulation. In these embodiments, desired viscosity or thickness of the product is maintained with a lesser amount than is typical of conventional thickeners. This is particularly desirable in products wherein the thickening agent antagonizes a desirable effect of another benefit agent, such as, for example, a conditioning agent. It is also desirable in products where one or more thickening agents are included for processing or formulation characteristics rather than for any desired benefit they provide to the portion of the body to which they are applied. In these cases, the copolymer may permit a decrease in the one or more thickening agents that possess antagonistic performance characteristics.

In a specific embodiment of the personal care product comprising the emulsion, the benefit comprises a conditioning benefit and the portion of the body comprises hair. Specific examples of the conditioning benefit include, but are not limited to an anti-static, lubricity, shine, viscosity, tactile, manageability, or a styling benefit. Non-limiting examples of manageability benefits include ease of dry and/or wet combing. Non-limiting examples of styling benefits include curl retention or hair-relaxing benefits. The conditioner may be a rinse-off or leave-in conditioner. In a specific embodiment the conditioning benefit comprises a curl-retention benefit.

Examples of suitable conditioning agents include, but are not limited to, cationic polymers, cationic surfactants, proteins, natural oils, silicones other than the copolymer, hydrocarbons, nonionic surfactants, amphoteric surfactants, or mixtures thereof. Examples of additional silicones which may be useful in the present personal care products include, but are not limited to: alkyl methyl siloxanes, cyclic siloxanes, gums, linear siloxanes, MQ siloxane resins, MTQ siloxane resins, and polyether siloxane copolymers.

Further embodiments of the present invention are direct to methods for providing a benefit to a portion of the body. One such method comprises administration of a safe and effective amount of a personal care product comprising the emulsion to a portion of the body. In one specific embodiment, a method of treating hair comprising administering a safe and effective amount of the emulsion is provided. A very specific embodiment provides a method of styling and holding hair comprising administering a safe and effective amount of the emulsion.

Formulating personal care products with the emulsion as described above may provide a thickening benefit. In a specific embodiment, an antiperspirant, hair, skin and color cosmetic products are provided. The antiperspirant product is formulated with the personal care composition comprising the emulsion as described above, wherein the benefit comprises a thickening benefit sufficient to maintain suspension of antiperspirant salts when the formulation comprises a substantially less than typical amount of conventional thickeners. In specific embodiments, the antiperspirant product is provided in the form of a solid, a soft solid or a gel. In a more specific embodiment the solid form comprises a soft solid or a gel.

Another specific embodiment provides a personal care product comprising the novel personal care composition where the benefit comprises an enhanced conditioning benefit and the portion of the body comprises skin. An embodiment directed to a method of treating skin is provided which comprises: (1) administration of a safe and effective amount of the personal care product comprising the emulsion; and (2) rubbing the safe and effective amount into the skin.

Another specific embodiment is directed to a color cosmetic product comprising the emulsion where the benefit comprises a cosmetic benefit. More specific embodiments are directed to liquid foundations.

In a specific embodiment, water in oil emulsion samples were prepared according to the following general procedure. The oil phase was prepared by mixing an emulsifier with an oil. The oil was isopropyl myristate or DOW CORNING® 200 Fluid, a silicone oil with a viscosity of 5 cSt, which is commercially available from Dow Corning Corporation. The emulsifier was a copolymer as described above. In each oil phase, the oil phase contained 10% emulsifier and 90% oil. The aqueous phase was prepared by mixing water and sodium chloride in a water: NaCl weight ratio of 99:1. Alternatively, the aqueous phase may comprise water, sodium chloride, and glycerol in a weight ratio (water:NaCl:glycerol) of 92.5:1.25:6.25. For each sample, the aqueous phase was added to the oil phase in increments. Between the addition of each increment, the sample was mixed for a period of time at 3400 revolutions per minute (rpm) in a DAC150 FlackTek™ SpeedMixer™ (commercially available from FlackTek, Inc. of Landrum, S.C., U.S.A.) to provide a coarse emulsion.

After all the aqueous phase was added, the resulting coarse emulsion was subjected to shear at ≥7,000 rpm in a homogenizer (T25 Digital ULTRA-TURRAX® commercially available from IKA of Wilmington, N.C., U.S.A.) to provide a fine emulsion The aqueous phase may be present in an amount ranging from 20% to 95%, alternatively 40 to 90%, and alternatively 60% to 80% by weight based on the weight of the emulsion.

Personal Care Applications

The emulsion described above is useful in personal care applications. When the emulsion described above is used in personal care applications, the emulsion may further comprise an additional ingredient, such as those described above. The additional ingredient may be selected from additional silicones, aerosols, anti-oxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sunscreening agents, suspending agents, tanning agents, other surfactants, thickeners, vitamins, botanicals, waxes, rheology-modifying agents, antiperspirants, anti-dandruff, anti-acne, anti-carie and wound healing-promotion agents, an additional oil, a hydrophilic medium, a filler, a fiber, a film forming polymer, an additional surfactant and/or emulsifier, a dyestuff, a structuring agent, an active ingredient, a fragrance, a preservative, and combinations thereof. Alternatively, the additional ingredient can be selected from an additional oil, a hydrophilic medium, a filler, a fiber, a film forming polymer, an additional surfactant and/or emulsifier, a dyestuff, a structuring agent, an active ingredient (such as a personal care active), a fragrance, a preservative, or a combination thereof.

Additional Oil

The additional oil may be another oil selected from the oils as described above, or the oil may be chosen from hydrocarbon-based oils, silicone oils and fluorinated oils. The oil may be chosen from volatile oils and non volatile oils, and mixtures thereof.

For purposes of this application, the term "hydrocarbon-based oil" means an oil formed essentially from, or even consisting of, carbon and hydrogen atoms, and possibly oxygen and nitrogen atoms, and containing no silicon or fluorine atoms; it may contain ester, ether, amine, or amide groups.

For purposes of this application, the term "silicone oil" means an oil containing at least one silicon atom, and alternatively containing Si—O— groups.

For purposes of this application, the term "fluorinated oil" means an oil containing at least one fluorine atom.

For purposes of this application, the term "volatile oil" means an oil (or non-aqueous medium) capable of evaporating on contact with the skin in less than one hour, at room temperature and atmospheric pressure. The volatile oil may be a volatile cosmetic oil, which is liquid at room temperature, especially having a non-zero vapor pressure, at room temperature and atmospheric pressure, in particular having a vapor pressure ranging from 0.13 Pa to 40 000 Pa (10~3 to 300 mmHg), alternatively ranging from 1.3 Pa to 13 000 Pa (0.01 to 100 mmHg) and alternatively ranging from 1.3 Pa to 1300 Pa (0.01 to 10 mmHg).

In addition, the volatile oil generally has a boiling point, measured at atmospheric pressure, ranging from 150° C. to 260° C. and alternatively ranging from 170° C. to 250° C.

The emulsion may comprise a volatile hydrocarbon-based oil chosen especially from hydrocarbon-based oils with a flash point ranging from 40° C. to 102° C., alternatively ranging from 40° C. to 55° C. and alternatively ranging from 40° C. to 50° C.

The volatile oil may be present in the emulsion in an amount ranging from 0.1% to 80% by weight, alternatively ranging from 1% to 70% by weight, and alternatively ranging from 5% to 50% by weight, relative to the total weight of the emulsion.

The emulsion may comprise at least one non-volatile oil in a non-volatile liquid fatty phase. The non-volatile oil may be present in an amount ranging from 0.1% to 80% by weight, alternatively ranging from 0.5% to 60% by weight, and alternatively ranging from 1% to 50% by weight relative to the total weight of the non-volatile liquid fatty phase.

The volatile hydrocarbon-based oils may be selected from hydrocarbon-based oils containing from 8 to 16 carbon atoms, and especially branched C8-C16 alkanes, for instance C8-C16 isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched C8-C16 esters and isohexyl neopentanoate, and combinations thereof.

Volatile oils that may also be used include volatile silicones, for instance volatile linear or cyclic silicone oils, especially those with a viscosity ≤8 centistokes ($8 \times 10^6$ m²/s) and especially containing from 2 to 7 silicon atoms, these silicones optionally comprising alkyl or alkoxy groups containing from 1 to 10 carbon atoms.

Volatile fluorinated solvents such as nonafluoromethoxybutane or perfluoromethylcyclopentane are also suitable for use in the composition.

Non-volatile hydrocarbon-based oils include, but are not limited to, hydrocarbon-based oils of plant origin, such as triesters of fatty acids and of glycerol, the fatty acids of which may have varied chain lengths from 4 to 24 carbon atoms, these chains possibly being linear or branched, and saturated or unsaturated. These oils are exemplified by wheat germ oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, marrow oil, blackcurrant oil, evening primrose oil, millet oil, barley oil, quinoa oil, rye oil, safflower oil, candlenut oil, passionflower oil or musk rose oil; or caprylic and/or capric acid triglycerides; synthetic ethers containing from 10 to 40 carbon atoms; apolar hydrocarbon-based oils, for instance squalene, linear or branched hydrocarbons such as liquid paraffin, liquid petroleum jelly and naphthalene oil, hydrogenated or partially hydrogenated polyisobutene, isoeicosane, squalane, decene/butene copolymers and polybutene/polyisobutene copolymers, and polydecenes, and mixtures thereof; synthetic esters, for instance oils of formula R'COOR" in which R' represents a linear or branched fatty acid residue containing from 1 to 40 carbon atoms and R" represents a hydrocarbon-based chain, which is especially branched, containing from 1 to 40 carbon atoms, on condition that R'+R">10, for instance cetostearyl octanoate, isopropyl myristate, isopropyl palmitate, alkyl benzoates of 12 to 15 carbon atoms, hexyl laurate, diisopropyl adipate, isononyl isononanoate, 2-ethylhexyl palmitate, isostearyl isostearate, alcohol or polyalcohol octanoates, decanoates or ricinoleates, for instance propylene glycol dioctanoate; hydroxylated esters, for instance isostearyl lactate or diisostearyl malate; and pentaerythritol esters; fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpenta-decanol; higher fatty acids such as oleic acid, linoleic acid or linolenic acid; carbonates; acetates; citrates; and combinations thereof.

The non-volatile silicone oils may be: non-volatile polydimethylsiloxanes (PDMS); polydimethylsiloxanes comprising alkyl or alkoxy groups, which are pendent and/or at the end of a silicone chain, these groups each containing from 3 to 40 carbon atoms; phenylsilicones; optionally fluorinated polyalkylmethylsiloxanes; polysiloxanes modified with fatty acids, fatty alcohols or polyoxyalkylenes, and combinations thereof. Alkylmethylsiloxanes, which generally will have the formula $Me_3SiO[Me_2SiO]_A[MeR'''SiO]_B SiMe_3$, in which R''' is a hydrocarbon group containing 6 to 30 carbon atoms, Me represents methyl, and the degree of polymerization (DP), i.e., the sum of A and B ranges from 3 to 50. Both the volatile and liquid species of alkymethysiloxanes can be used in the composition.

The oil may alternatively comprise a silicone carbinol. These materials are described in WO 03/101412 A2, and can be commonly described as substituted hydrocarbyl functional siloxane fluids or resins.

The emulsion may contain an oil with a molar mass ranging from 650 to 10,000 g/mol, which may be selected from: lipophilic polymers such as polybutylenes; polyisobutylenes, for example hydrogenated polyisobutylenes; polydecenes and hydrogenated polydecenes; vinylpyrrolidone copolymers such as a vinylpyrrolidone/1-hexadecene copolymer (MM=7300 g/mol); esters such as linear fatty acid esters with a total carbon number ranging from 35 to 70, for instance pentaerythrityl tetrapelargonate; hydroxylated esters such as polyglyceryl-2 triisostearate; aromatic esters such as tridecyl trimellitate; and pentaerythritol esters, and triisoarachidyl citrate, pentaerythrityl tetraisononanoate, glyceryl triisostearate, glyceryl tris (2-decyl)tetradecanoate, pentaerythrityl tetraisostearate, polyglyceryl-2 tetraisostearate, and combinations thereof.

The emulsion may comprise a fluid silicone compound such as a silicone gum or a silicone oil of high viscosity.

A polydimethylsiloxane with a viscosity at 25° C. ranging from 10 to 10,000,000 cSt., alternatively 1,000 to 2,500,000 cSt., alternatively 5,000 to 1,000,000 cSt., and alternatively 10,000 to 60,000 cSt. may be selected.

The weight-average molecular mass of the fluid silicone may range from 1,000 to 1, 500,000 g/mol, alternatively 200,000 to 1,000,000 g/mol.

The oil phase of the emulsion can also contain silicone elastomer gels, elastomeric solid organopolysiloxane enclosed in a fatty phase, where at least one elastomeric solid organopolysiloxane is at least partially crosslinked. Examples of such elastomeric solid organopolysiloxane are described in the following Patents and Patent Publications U.S. Pat. No. 5,654,362, EP 848029, EP 869142, WO2007109240, WO2007109260, WO2007109282, WO2009006091, WO2010080755, U.S. Pat. No. 4,987,169, and U.S. Pat. No. 5,760,116. These elastomer gels can be non emulsifying or self emulsifying or a combination of both.

Hydrophilic Medium

The aqueous phase of the emulsion may comprise a hydrophilic medium comprising water or a mixture of water and a hydrophilic organic solvent, for instance alcohols, such as linear or branched lower monoalcohols containing from 2 to 5 carbon atoms, for instance ethanol, isopropanol or n-propanol, and polyols, for instance glycerol, diglycerol, propylene glycol, sorbitol, pentylene glycol and polyethylene glycols, or alternatively hydrophilic C2 ethers and $C_2$-$C_4$ aldehydes.

The water or the mixture of water and of hydrophilic organic solvents may be present in the emulsion in an amount ranging from 0.1% to 95% by weight and alternatively ranging from 10% to 80% by weight relative to the total weight of the emulsion.

Fillers

The filler suitable for use in the emulsion described herein may be mineral or organic, of any form, platelet-shaped, spherical or oblong, irrespective of the crystallographic form (for example lamellar, cubic, hexagonal, orthorhombic, etc.). Examples include talc, mica, silica, kaolin, polyamide, poly-β-alanine powder and polyethylene powder, tetrafluoroethylene polymer powders, lauroyllysine, starch, boron nitride, hollow polymer microspheres, acrylic acid copolymers, silicone resin microbeads, elastomeric polyorganosiloxane particles, precipitated calcium carbonate, magnesium carbonate, magnesium hydrogen carbonate, hydroxyapatite, hollow silica microspheres, glass or ceramic microcapsules, and metal soaps for example zinc stearate, magnesium stearate, lithium stearate, zinc laurate or magnesium myristate, polymethyl methacrylate powders. Alternatively, the filler may be a polyurethane powder.

Alternatively, the filler may be an elastomeric organopolysiloxane powder. Advantageously, the elastomeric organopolysiloxane is non-emulsifying. Spherical elastomeric organopolysiloxanes are described in patent applications JP-A-61-194 009, EP-A-242 219, EP-A-295 886 and EP-A-765 656. The organopolysiloxane powders can also mixed with other particles as described in patent publication U.S. Pat. No. 7,399,803.

The elastomeric organopolysiloxane powder may comprise at least one elastomeric organopolysiloxane powder coated with silicone resin, such as with silsesquioxane resin, as described, for example, in patent U.S. Pat. No. 5,538,793.

Other elastomeric organopolysiloxanes in the form of spherical powders may be hybrid silicone powders functionalized with fluoroalkyl groups or hybrid silicone powders functionalized with phenyl groups.

The filler may be an N-acylamino acid powder. The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The amino acid may be, for example, lysine, glutamic acid or alanine.

When present, the filler may be added to the emulsion in an amount ranging from 0.01% to 30% by weight.

Fibers

For purposes of this application, the term "fiber" means an object of length L and diameter D such that L is very much greater than D, D being the diameter of the circle in which the cross section of the fiber is inscribed.

In particular, the ratio L/D (or shape factor) ranges from 3.5 to 2500, alternatively 5 to 500, and alternatively 5 to 150.

The fiber that may be used in the emulsion may be fibers of synthetic or natural, mineral or organic origin. The fiber that may be used in the emulsion may be selected from polyamide, cellulose, poly-p-phenylene-terephthamide or polyethylene fibers. Polyethylene fibers may also be used.

The fibers may be present in the emulsion in an amount ranging from 0.01% to 10% by weight.

Film-Forming Polymer

Certain film-forming polymers may be gelling agents. For the purposes of this application, the term "film-forming polymer" means a compound containing at least two repeating units and alternatively at least three repeating units, where said compound is capable, by itself or in the presence of an auxiliary film-forming agent, of forming a macroscopically continuous film on a support, especially on keratin materials, alternatively a cohesive film and alternatively a film with cohesion and mechanical properties such that said film can be isolated from said support.

In one embodiment, the film-forming polymer is a film forming organic polymer chosen from the group comprising: film-forming polymers that are soluble in an organic liquid medium, in particular liposoluble polymers, when the organic liquid medium comprises at least one oil; film-forming polymers that are dispersible in an organic solvent medium, in particular polymers in the form of non-aqueous dispersions of polymer particles, preferably dispersions in silicone oils or hydrocarbon-based oils.

Alternatively, the film-forming polymers that may be used in the emulsion may include synthetic polymers, of free-radical type or of polycondensate type, polymers of natural origin, and mixtures thereof. Such film-forming polymers include acrylic polymers, polyurethanes, polyesters, polyamides, polyureas, cellulose-based polymers, for instance nitrocellulose, silicone polymers, in particular silicone resins, silicone-grafted acrylic polymers, polyamide polymers and copolymers, and polyisoprenes.

The composition according to the invention may comprise, as film-forming polymer, a dispersion of particles of a grafted ethylenic polymer in the fatty phase.

Silicone-based macromonomers that may be used as the film forming polymer include polydimethylsiloxanes containing mono(meth)acrylate end groups. Silicone-based macromonomers that may be used include monomethacryloxypropyl polydimethylsiloxanes.

Alternatively, the emulsion may contain, as film-forming polymer, a linear block ethylenic polymer, referred to hereinbelow as a "block polymer". For purposes of this application, the term "block polymer" means a polymer comprising at least two different blocks and preferably at least three different blocks.

The polymer may be a polymer of linear structure. Alternatively, a polymer of non-linear structure is, for example, a polymer of branched, star, grafted or other structure may be used.

In one embodiment, the film forming polymer comprises at least three different blocks, and the first and second blocks of the block polymer are mutually incompatible.

In one embodiment, the film-forming polymer is an organic film-forming polymer that is soluble in the fatty phase, which comprises a liquid phase comprising at least one oil.

The liposoluble film forming polymer may be of any chemical type and may especially be chosen from: a) liposoluble, amorphous homopolymers and copolymers of olefins, of cycloolefins, of butadiene, of isoprene, of styrene, of vinyl ethers, esters or amides, or of (meth)acrylic acid esters or amides comprising a linear, branched or cyclic alkyl group of 4 to 50 carbon atoms, and which may be amorphous. The liposoluble homopolymers and copolymers may be obtained from monomers selected from the group consisting of isooctyl (meth)acrylate, isononyl (meth)acrylate, 2-ethylhexyl (meth)acrylate, lauryl (meth)acrylate, isopentyl (meth)acrylate, n-butyl (meth)acrylate, isobutyl (meth)acrylate, methyl (meth)acrylate, tert-butyl (meth)acrylate, tridecyl (meth)acrylate and stearyl (meth)acrylate, or combinations thereof.

Particular liposoluble copolymers that may be used include: i) acrylic-silicone grafted polymers containing a silicone backbone and acrylic grafts or containing an acrylic backbone and silicone grafts, such as the product sold under the name SA 70.5 by 3M and described in patents U.S. Pat. No. 5,725,882; U.S. Pat. No. 5,209,924; U.S. Pat. No. 4,972,037; U.S. Pat. No. 4,981,903; U.S. Pat. No. 4,981,902 and U.S. Pat. No. 5,468,477, and in patents U.S. Pat. No. 5,219,560 and EP 0 388 582; ii) liposoluble polymers bearing fluoro groups, belonging to one of the classes described above, in particular the Fomblin products described in patent U.S. Pat. No. 5,948,393 and the alkyl (meth)acrylate/per-fluoroalkyl (meth)acrylate copolymers described in patents EP 0 815 836 and U.S. Pat. No. 5,849,318; iii) polymers or copolymers resulting from the polymerization or copolymerization of an ethylenic monomer, comprising one or more ethylenic bonds, which may be conjugated (or dienes). A s polymers or copolymers resulting from the polymerization or copolymerization of an ethylenic monomer, it is possible to use vinyl, acrylic or methacrylic copolymers.

In one embodiment, the film-forming polymer is a block copolymer comprising at least one block consisting of styrene units or styrene derivatives (for example methylstyrene, chlorostyrene or chloromethylstyrene).

In one embodiment, the film-forming polymer is selected from copolymers of a vinyl ester (the vinyl group being directly attached to the oxygen atom of the ester group and the vinyl ester having a saturated, linear or branched hydrocarbon-based radical of 1 to 19 carbon atoms, linked to the carbonyl of the ester group) and of at least one other monomer, which may be a vinyl ester (other than the vinyl ester already present), an α-olefin (containing from 8 to 28 carbon atoms), an alkyl vinyl ether (the alkyl group of which contains from 2 to 18 carbon atoms) or an allylic or methallylic ester (containing a saturated, linear or branched hydrocarbon-based radical of 1 to 19 carbon atoms, linked to the carbonyl of the ester group).

These copolymers may be partially crosslinked using crosslinking agents, which may be either of the vinyl type or of the allylic or methallylic type, such as tetraallyloxyethane, divinylbenzene, divinyl octanedioate, divinyl dodecanedioate, and divinyl octadecanedioate.

Liposoluble film-forming polymers that may also be mentioned include liposoluble copolymers, such as those resulting from the copolymerization of vinyl esters containing from 9 to 22 carbon atoms or of alkyl acrylates or methacrylates, the alkyl radicals containing from 10 to 20 carbon atoms.

Such liposoluble copolymers may be selected from copolymers of polyvinyl stearate, polyvinyl stearate crosslinked with divinylbenzene, with diallyl ether or with diallyl phthalate, polystearyl (meth)acrylate copolymers, polyvinyl laurate and polylauryl (meth)acrylate copolymers, these poly(meth)acrylates possibly being crosslinked with ethylene glycol dimethacrylate or tetraethylene glycol dimethacrylate.

Amorphous and liposoluble polycondensates, preferably not comprising any groups donating hydrogen interactions, in particular aliphatic polyesters containing C4-50 alkyl side chains or polyesters resulting from the condensation of fatty acid dimers, or even polyesters comprising a silicone-based segment in the form of a block, graft or end group, as defined in patent application FR 0 113 920.

Amorphous and liposoluble polysaccharides comprising alkyl (ether or ester) side chains, in particular alkylcelluloses containing a saturated or unsaturated, linear or branched C1 to C8 alkyl radical, such as ethylcellulose and propylcellulose.

Alternatively, the film-forming polymer may be selected from cellulose-based polymers such as nitrocellulose, cellulose acetate, cellulose acetobutyrate, cellulose acetopropionate or ethylcellulose, or from polyurethanes, acrylic polymers, vinyl polymers, poly vinyl butyrals, alkyd resins, resins derived from aldehyde condensation products, such as arylsulfonamide-formaldehyde resins, for instance toluenesulfonamide-formaldehyde resin, and aryl sulfonamide epoxy resins.

Alternatively, the film forming polymer may be a silicone resin. For purposes of this application, the term "resin" means a three-dimensional structure. In one embodiment, the silicone resin is selected from silsesquioxanes and siloxysilicates. In one embodiment, the silicone resin is selected from siloxysilicates, such as trimethyl siloxysilicates, which are represented by the following formula: $[R^{16}_3SiO_{1/2}]_E(SiO_{4/2})_F$ (units M and Q), in which subscripts E and F may each independently have values ranging from 50 to 80, and $R^{16}$ represents an alkyl, such as a methyl or an alkyl of two or more carbon atoms. The ratio of the units M to the units Q may range from 0.7 to 1.

Alternatively, the silicone resin may be selected from silsesquioxanes comprising T units of formula: $[R^{17}SiO_{3/2}]_G$, in which subscript G has a value that may range up to several thousand and $R^{17}$ represents an alkyl, such as a methyl or an alkyl of two or more carbon atoms. In one embodiment, the silsesquioxane is selected from polymethylsilsesquioxanes, which are silsesquioxanes such that $R^{17}$ is a methyl group or a propyl group (polypropylsilsesquioxane). The polymethylsilsesquioxanes may comprise, for example, less than 500 T units, and alternatively 50 to 500 T units.

In one embodiment of the invention, the silicone resin is soluble or dispersible in silicone oils or volatile organic liquids. In one embodiment, the silicone resin is solid at 25° C.

In one embodiment, the silicone resin may have a molecular mass ranging from 1,000 to 10,000 grams/mol.

In another embodiment, the film-forming silicone resin is a copolymer, in which at least one unit of the copolymer is chosen from the silicone units M, D, T and Q, and in which at least one additional unit of the copolymer is chosen from esters.

In a non-limiting manner, the film-forming polymers may be chosen from the following polymers or copolymers: polyurethanes, polyurethane-acrylics, polyureas, polyurea-polyurethanes, polyester-polyurethanes, polyether-polyurethanes, polyesters, polyesteramides, alkyds; acrylic and/or vinyl polymers or copolymers; acrylic-silicone copolymers; polyacrylamides; silicone polymers, for instance silicone polyurethanes or silicone acrylics, and fluoro polymers, and mixtures thereof.

The film forming polymer may be a vinyl polymer comprising at least one carbosiloxane dendrimer-based unit. The vinyl polymer may especially have a backbone and at least one side chain, which comprises a carbosiloxane dendrimer structure. For purposes of this application, the term "carbosiloxane dendrimer structure" represents a molecular structure with branched groups of high molecular masses with high regularity in the radial direction starting from the backbone bond. Such carbosiloxane dendrimer structures are described in the form of a highly branched siloxane-silylalkylene copolymer in the laid-open Japanese patent application Kokai 9-171154.

The vinyl polymer may be one of the polymers described in the examples of patent application EP 0 963 751, or a polymer obtained according to the process described in the said patent application.

According to one embodiment, the vinyl polymer may further comprise at least one organofluorine group. The fluoro vinyl polymer may be one of the polymers described in the examples of patent application WO 03/045 337, or one of polymers obtained according to the process described in said patent application.

According to one embodiment, the grafted vinyl polymers are borne in an oil, which is may be volatile, selected from silicone oils and/or hydrocarbon-based oils. According to one embodiment, the silicone oil may be cyclopentasiloxane. Alternatively, the hydrocarbon-based oil may be isododecane. The emulsion may comprise at least one polyamide polymer or copolymer, which may be selected from polyamide homopolymers, polyamides branched with fatty chains, polyamide-organosiloxanes, polyamide-polyester copolymers and polyamide-polyacrylic copolymers, and mixtures thereof.

As polyamide polymers that may be used in the emulsion, mention may also be made of polyamides comprising at least one polyorganosiloxane group, containing 1 to 1,000 organosiloxane units in the main chain or in the form of a graft. The polyamide polymers are, for example, those described in documents U.S. Pat. No. 5,874,069, U.S. Pat. No. 5,919,444, U.S. Pat. No. 6,051,216, U.S. Pat. No. 5,981,680 and WO 04/054 524.

The emulsion may comprise a semi-crystalline polymer, which may have a melting point of greater than or equal to 30° C. The melting point values correspond to the melting point measured using a differential scanning calorimeter (DSC) such as the calorimeter sold under the name DSC 30 by Mettler, with a temperature rise of 5 or 10° C. per minute. (The melting point considered is the point corresponding to the temperature of the most endothermic peak in the thermogram). The semi-crystalline polymer comprises at least one crystallizable pendent chain or at least one crystallizable block. Aside from the crystallizable chains or blocks, the polymer blocks are amorphous. For the purposes of the invention, the term "crystallizable chain or block" means a chain or block which, if it was alone, would change from the amorphous state to the crystalline state reversibly, depending on whether it is above or below the melting point. For the purposes of this application, a chain is a group of atoms that are pendent or lateral relative to the polymer backbone. A block is a group of atoms belonging to the backbone, this group constituting one of the repeating units of the polymer. The semi-crystalline polymers that may be used in the invention are exemplified by polyolefin block copolymers of controlled crystallization, the monomers of which are described in EP-A-0 951 897.

The film forming polymer, when present, may be in the emulsion in an amount ranging from 0.1% to 30% by weight.

Additional Surfactants/Emulsifiers

The emulsion may further comprise an additional surfactant or emulsifier. The additional surfactant or emulsifier may be solid at room temperature, which may be a block polymer, a grafted polymer and/or a random polymer, alone or in combination of two or more. Among the grafted polymers that may be mentioned are silicone polymers grafted with a hydrocarbon-based chain and hydrocarbon-based polymers grafted with a silicone chain.

Thus, grafted-block or block copolymers comprising at least one block of polyorganosiloxane type and at least one block of a free-radical polymer, for instance grafted copolymers of acrylic/silicone type, may be used, which may be used especially when the non-aqueous medium contains silicone.

It is also possible to use grafted-block or block copolymers comprising at least one block of polyorganosiloxane type and at least one block of a polyether. The polyorganopolysiloxane block may be a polydimethylsiloxane or a poly (C2-C18) alkylmethylsiloxane; the polyether block may be a poly (C2-C18) alkylene, such as polyoxyethylene and/or polyoxypropylene. In particular, dimethicone copolyols or (C2-C18) alkyldimethicone copolyols may be used.

Water soluble or water dispersible silicone polyether compositions may be included in the present emulsions. These are also known as polyalkylene oxide silicone copolymers, silicone poly (oxyalkylene) copolymers, silicone glycol copolymers, or silicone surfactants. These can be linear, rake, or graft type materials, or ABA type where the B is the siloxane polymer block, and the A is the poly (oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible. Another type of silicone polyether composition that may be included in the present composition is an ABn polyalkylene oxide silicone copolymers as described in EP 0 492 657.

The additional emulsifier or surfactant may be selected from nonionic, anionic, cationic and amphoteric surfactants or combinations thereof. Reference may be made to Kirk-Othmer's "Encyclopedia of Chemical Technology", volume 22, pp. 333-432, 3rd edition, 1979, Wiley, for the definition of the properties and (emulsifying) functions of surfactants, in particular pp. 347-377 of this reference, for anionic, amphoteric and nonionic surfactants.

Nonionic surfactants may be comprise: oxyethylenated and/or oxypropylenated ethers (which may comprise from 1 to 150 oxyethylene and/or oxypropylene groups) of glycerol; oxyethylenated and/or oxypropylenated ethers (which may comprise from 1 to 150 oxyethylene and/or oxypropylene groups) of fatty alcohols (especially of a C8-C24 and alternatively C12-C18 alcohol), such as oxyethylenated cetearyl alcohol ether containing 30 oxyethylene groups (CTFA name Ceteareth-30) and the oxyethylenated ether of the mixture of C12-C15 fatty alcohols comprising 7 oxyethylene groups (CTFA name C12-15 Pareth-7); fatty acid esters (such as a C8-C24 and alternatively C16-C22 acid) of polyethylene glycol (which may comprise from 1 to 150 ethylene glycol units), such as PEG-50 stearate and PEG-40 monostearate; fatty acid esters (especially of a C8-C24 and preferably C16-C22 acid) of oxyethylenated and/or oxypropylenated glyceryl ethers (which may comprise from 1 to 150 oxyethylene and/or oxypropylene groups), for instance PEG-200 glyceryl monostearate; glyceryl stearate polyethoxylated with 30 ethylene oxide groups, glyceryl oleate polyethoxylated with 30 ethylene oxide groups, glyceryl cocoate polyethoxylated with 30 ethylene oxide groups, glyceryl isostearate polyethoxylated with 30 ethylene oxide groups, and glyceryl laurate polyethoxylated with 30 ethylene oxide groups; fatty acid esters (especially of a C8-C24 and preferably C16-C22 acid) of oxyethylenated and/or oxypropylenated sorbitol ethers (which may comprise from 1 to 150 oxyethylene and/or oxypropylene groups); dimethicone copolyol benzoate; copolymers of propylene oxide and of ethylene oxide, also known as EO/PO polycondensates; and mixtures thereof; saccharide esters and ethers, such as sucrose stearate, sucrose cocoate and sorbitan stearate, and mixtures thereof, fatty acid esters (such as a C8-C24 and alternatively C16-C22 acid) of polyols, especially of glycerol or of sorbitol, such as glyceryl stearate, glyceryl stearate, glyceryl laurate, polyglyceryl-2 stearate, sorbitan tristearate or glyceryl ricinoleate.

Anionic surfactants include C16-C30 fatty acid salts, such as those derived from amines, for instance triethanolamine stearate; polyoxyethylenated fatty acid salts, such as those derived from amines or alkali metal salts, and combinations thereof; phosphoric esters and salts thereof, such as DEA oleth-10 phosphate or monocetyl monopotassium phosphate sulfosuccinates such as Disodium PEG-5 citrate lauryl sulfosuccinate and Disodium ricinoleamido MEA sulfosuccinate; alkyl ether sulfates, such as sodium lauryl ether sulfate; isethionates; acylglutamates such as disodium hydrogenated tallow glutamate, alkyl polyglucosides and combinations thereof.

The emulsion may further comprise an amphoteric surfactant, for instance N-acylamino acids such as N-alkylaminoacetates and disodium cocoamphodiacetate, and amine oxides such as stearamine oxide, or alternatively silicone surfactants, for instance dimethicone copolyol phosphates.

Dyestuffs

The emulsion may further comprise a dyestuff. The dyestuff may be selected from pulverulent dyestuffs (such as pigments and nacres) and water-soluble dyestuffs. For purposes of this application, the term "pigments" means white or colored, mineral or organic particles of any form, which are insoluble in the physiological medium, and which are intended to color the emulsion. For purposes of this application, the term "nacres" means iridescent particles of any form, produced especially by certain molluscs in their shell, or else synthesized.

The pigments may be white or colored, and mineral and/or organic. The mineral pigments include titanium dioxide, optionally surface-treated, zirconium oxide or cerium oxide, zinc oxide, iron oxide (black, yellow or red), chromium oxide, manganese violet, ultramarine blue, chromium hydrate, ferric blue, and metal powders, for instance aluminum powder or copper powder. The organic pigments include carbon black, pigments of D & C type, and lakes based on cochineal carmine or on barium, strontium, calcium or aluminum.

Mention may also be made of pigments with an effect, such as particles comprising a natural or synthetic, organic or mineral substrate, for example glass, acrylic resins, polyester, polyurethane, polyethylene terephthalate, ceramics or aluminas, said substrate being uncoated or coated with metallic substances, for instance aluminum, gold, silver, platinum, copper or bronze, or with metal oxides, for instance titanium dioxide, iron oxide or chromium oxide, and combinations thereof.

The nacres may be chosen from white nacreous pigments such as mica coated with titanium or with bismuth oxychloride, colored nacreous pigments such as titanium mica coated with iron oxides, titanium mica coated with ferric blue or with chromium oxide, titanium mica coated with an organic pigment of the abovementioned type, and also nacreous pigments based on bismuth oxychloride. Interference pigments, such as liquid-crystal or multilayer interference pigments, may alternatively be used.

Structuring Agents

The emulsion may further comprise a structuring agent. For purposes of this application, the term "structuring agent" means a compound capable of increasing the viscosity of the emulsion. The structuring agent makes it possible to obtain an emulsion that can have a texture ranging from fluid to solid textures.

The structuring agent may be present in the emulsion in an amount ranging from 0.1% to 20% by weight, alternatively ranging from 0.1% to 15% by weight and alternatively ranging from 0.5% to 10% by weight, relative to the total weight of the emulsion.

The structuring agent may be selected from thickeners (oily-medium thickeners; aqueous-medium thickeners), organogelling agents, waxes, pasty compounds and gums.

The aqueous-medium thickener may be chosen from: hydrophilic clays, hydrophilic fumed silica, water-soluble cellulose-based thickeners, guar gum, xanthan gum, carob gum, scleroglucan gum, gellan gum, rhamsan gum, karaya gum or carrageenan gum, alginates, maltodextrins, starch and its derivatives, and hyaluronic acid and its salts, the polyglyceryl (meth)acrylate polymers sold under the names Hispagel or Lubragel by Hispano Quimica or Guardian, polyvinylpyrrolidone, polyvinyl alcohol, crosslinked acrylamide polymers and copolymers, or alternatively the crosslinked methacryloyloxyethyltrimethylammonium chloride homopolymers, associative polymers and especially associative polyurethanes and sodium acrylate blends. Such thickeners are described especially in patent application EP-A-1 400 234.

The oily-medium thickener may be chosen from: organophilic clays; hydrophobic fumed silicas; alkyl guar gums (with a C1-C6 alkyl group), such as those described in EP-A-708 114; oil-gelling polymers, for instance triblock polymers or star polymers resulting from the polymerization or copolymerization of at least one monomer containing an ethylenic group.

Alternatively, the structuring agent can be a wax. For the purposes of this application, the term "wax" means a lipophilic compound that is solid at room temperature (25° C.), which undergoes a reversible solid/liquid change of state, and which has a melting point of greater than or equal to 30° C., which may be up to 120° C.

The waxes may be hydrocarbon-based waxes, fluoro waxes and/or silicone waxes, and may be of plant, mineral, animal and/or synthetic origin. In particular, the waxes may have a melting point of greater than 30° C.

Suitable waxes include beeswax, carnauba wax or candelilla wax, paraffin, microcrystalline waxes, ceresin or ozokerite; synthetic waxes, for instance polyethylene waxes or Fischer-Tropsch waxes, and silicone waxes, for instance alkyl, alkoxy dimethicones containing from 16 to 45 carbon atoms or silsesquioxane resin wax as described in patent application publication WO2005100444.

Alternatively, the emulsion may contain a pasty compound, which may be selected from lanolin and its derivatives; polymeric or non-polymeric silicone compounds; polymeric or non-polymeric fluoro compounds; vinyl polymers, such as olefin homopolymers, olefin copolymers, hydrogenated diene homopolymers, and linear or branched oligomers, homopolymers or copolymers of alkyl (meth) acrylates, such as those containing a C8-C30 alkyl group; oligomers, homopolymers, and copolymers of vinyl esters containing C8-C30 alkyl groups; oligomers, homopolymers and copolymers of vinyl ethers containing C8-C30 alkyl groups; liposoluble polyethers resulting from the polyetherification between one or more C2-C100 (alternatively C2-C50) diols, esters, and combinations thereof. The esters include esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid. The pasty compounds of plant origin include a mixture of soybean sterols and of oxyethylenated (5 OE) oxypropylenated (5 OP) pentaerythritol.

Active Ingredients

As used herein, a "personal care active" means any compound or combination of compounds that are known in the art as additives in the personal care formulations that are typically added for the purpose of treating hair or skin to provide a cosmetic and/or aesthetic benefit. A "healthcare active" means any compound or mixtures of compounds that are known in the art to provide a pharmaceutical or medical benefit. Thus, "healthcare active" include materials consider as an active ingredient or active drug ingredient as generally used and defined by the United States Department of Health & Human Services Food and Drug Administration, contained in Title 21, Chapter I, of the Code of Federal Regulations, Parts 200-299 and Parts 300-499.

Some representative examples of active ingredients include; drugs, vitamins, minerals; hormones; topical antimicrobial agents such as antibiotic active ingredients, antifungal active ingredients for the treatment of athlete's foot, jock itch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and sunburn prevention and treatment agents.

Useful active ingredients for use in the emulsion include vitamins and their derivatives, including "pro-vitamins". Vitamins useful herein include, but are not limited to, Vitamin $A_1$, retinol, C2 to C18 esters of retinol, vitamin E, tocopherol, esters of vitamin E, and combinations thereof. Retinol includes trans-retinol, 1,3-cis-retinol, 11-cis-retinol, 9-cis-retinol, and 3,4-didehydro-retinol, Vitamin C and its derivatives, Vitamin $B_1$, Vitamin $B_2$, Pro Vitamin B5, panthenol, Vitamin $B_6$, Vitamin $B_{12}$, niacin, folic acid, biotin, and pantothenic acid. Other suitable vitamins and the International Nomenclature Cosmetic Ingredient Name (INCI) names for the vitamins considered included herein are ascorbyl dipalmitate, ascorbyl methylsilanol pectinate, ascorbyl palmitate, ascorbyl stearate, ascorbyl glucocide, sodium ascorbyl phosphate, sodium ascorbate, disodium ascorbyl sulfate, potassium (ascorbyl/tocopheryl) phosphate.

Alternatively, the active ingredient used in the emulsion can be an active drug ingredient. Representative examples of some suitable active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, vincristine, bleomycin sulfate, aurothioglucose, suramin, mebendazole, clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, salbutamol, guanabenz, labetalol, pheniramine, metrifonate, and steroids.

Considered to be included herein as active drug ingredients for purposes of this application are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anesthetic agents such as lidocaine; antipruritic agents; antidermatitis agents; and agents generally considered barrier films.

Alternatively, the active ingredient in the emulsion can be a protein, such as an enzyme. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha or beta), lipases, mannanases, cellulases, collagenases, lisozymes, superoxide dismutase, catalase, and mixtures thereof. Said proteases include, but are not limited to, trypsin, chymotrypsin, pepsin, pancreatin and other mammalian enzymes; papain, bromelain and other botanical enzymes; subtilisin, epidermin, nisin, naringinase (L-rhammnosidase) urokinase and other bacterial enzymes. Said lipases include, but are not limited to, triacyl-glycerol lipases, monoacyl-glycerol lipases, lipoprotein lipases, e.g., steapsin, erepsin, pepsin, other mammalian, botanical, bacterial lipases and purified ones. Natural papain is useful as said enzyme. Further, stimulating hormones, e.g., insulin, can be used together with these enzymes to boost the effectiveness of them.

Alternatively, the active ingredient may be a sunscreen agent. The sunscreen agent can be selected from any sunscreen agent known in the art to protect skin from the harmful effects of exposure to sunlight. The sunscreen agent may be selected from an organic compound, an inorganic compound, or a combination thereof that absorbs ultraviolet (UV) light. Representative, non-limiting examples that can be used as the sunscreen agent include; Aminobenzoic Acid, Cinoxate, Diethanolamine Methoxycinnamate, Digalloyl Trioleate, Dioxybenzone, Ethyl 4-[bis(Hydroxypropyl)] Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoylmethane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxybenzophenone-1 Copolymer. These sunscreen agents can be selected as one or a combination of two or more.

Alternatively, the active ingredient may a plant extract. Alternatively, the active ingredient may be a self tanning agent such as but not limited to dihydroxyacetone and erythrulose or an insect repellent such as but not limited to ethyl butylacetylaminopropionate or plant extract such as citronella. The amount of active ingredient present in the emulsion will vary depending on factors including the type of active ingredient selected and the method of use of the emulsion, however, the amount of active ingredient may range from 0.05 wt % to 50 wt %, alternatively 1 wt % to 25 wt %, or alternatively 1 to 10 wt %, based on the weight of the emulsion.

Alternatively, the active ingredient may be an antiperspirant and/or deodorant agent. Some examples of antiperspirant agents and deodorant agents are Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, and Zinc Ricinoleate.

Fragrance

Fragrance or perfume can also be added to the emulsion. The fragrance can be any perfume or fragrance ingredient commonly used in the perfume industry. These fragrance ingredients may belong to a variety of chemical classes, as varied as alcohols, aldehydes, ketones, esters, ethers, acetates, nitrites, terpenic hydrocarbons, heterocyclic nitrogen or sulfur containing compounds, as well as essential oils of natural or synthetic origin. Many of these fragrance ingredients are described in detail in standard textbook references such as Perfume and Flavour Chemicals, 1969, S. Arctander, Montclair, N.J.

Preservatives

When making an emulsion with the emulsifiers described herein, it may be desirable to add various preservatives such as the parabens, BHT, BHA, phenoxy ethanol, as listed on the Annex VI, Part 1 of the European Cosmetic directive—LIST OF PRESERVATIVES WHICH COSMETIC PRODUCTS MAY CONTAIN. When present, the amount of preservative may range from 0.01% to 5% by weight based on the weight of the emulsion.

The emulsion is suitable for use in personal care products. Such personal care products are exemplified by antiperspirants and deodorants, skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, wrinkle fillers, skin imperfection hiders, skin surface smoothers, eyelash curlers, nail varnishes, hair make-up products, eye shadows, body makeups, and powders, medicament creams, pastes or sprays including anti-acne, dental hygienic, antibiotic, healing promotive, nutritive and the like, which may be preventative and/or therapeutic.

EXAMPLES

The following examples are included to demonstrate the invention to one of ordinary skill. However, those of ordinary skill in the art should, in light of the present disclosure, appreciate that many changes can be made in the specific embodiments which are disclosed and still obtain a like or similar result without departing from the spirit and scope of the invention. All amounts, ratios, and percentages are by weight unless otherwise indicated.

Reference Example 1A

Long Chain Copolymer Synthesis

In a 1000 ml glass reactor equipped with stirrer, temperature controller, and reflux condenser the copolymer was prepared by first reacting 125 g trimethylsiloxy terminated poly(dimethyl/methyl(aminoethylaminoisobutyl)siloxane), with a DP of 380 and 8 to 10 aminoethylaminoisobutyl groups per molecule with 3.57 g of gluconolactone, which was an amount sufficient to react with half of the primary amines on the poly(dimethyl/methyl(aminoethylaminoisobutyl)siloxane). This reaction was performed in the presence of 129 g ethanol at a temperature of 74° C. In a second step, the resulting polymer was reacted with a mixture of dodecylglycidyl ether and tetradecylgycidyl ether. This second step reaction was also carried out in the presence of ethanol at 74° C.

After the completion of the reaction, 385.7 g of Isopropyl Myristate emollient was added to the reaction mixture, then the ethanol solvent was stripped out at a temperature of 74° C. under full vacuum.

Reference Example 1B

Long Chain Copolymer Synthesis

In a 1000 ml glass reactor equipped with stirrer, temperature controller, and reflux condenser the copolymer was prepared by first reacting 125 g trimethylsiloxy terminated poly(dimethyl/methyl(aminoethylaminoisobutyl)siloxane), with a DP of 380 and 8 to 10 aminoethylaminoisobutyl groups per molecule with 3.57 g of gluconolactone, which was an amount sufficient to react with half of the primary amines on the poly(dimethyl/methyl(aminoethylaminoisobutyl)siloxane). This reaction was performed in the presence of 129 g ethanol at a temperature of 74° C. In a second step, the resulting polymer was reacted with a mixture of dodecylglycidyl ether and tetradecylgycidyl ether. This second step reaction was also carried out in the presence of ethanol at 74° C.

After the completion of the reaction, 385.7 g of 5 cSt 200 Fluid emollient was added to the reaction mixture, then the ethanol solvent was stripped out at a temperature of 74° C. under full vacuum. The reaction scheme was as follows for the second step in both reference 1A and 1B:

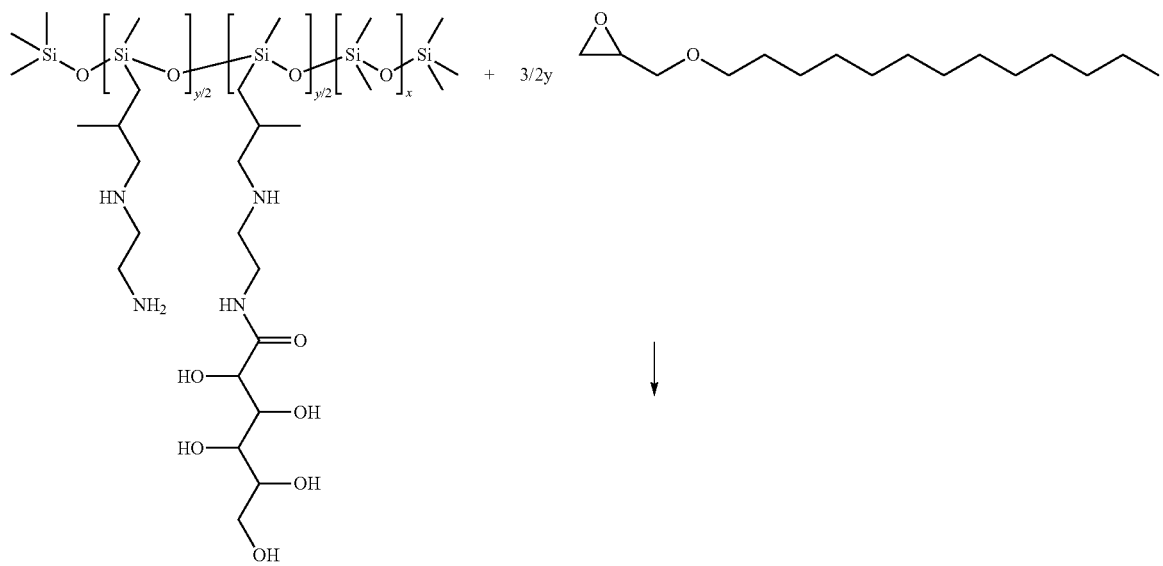

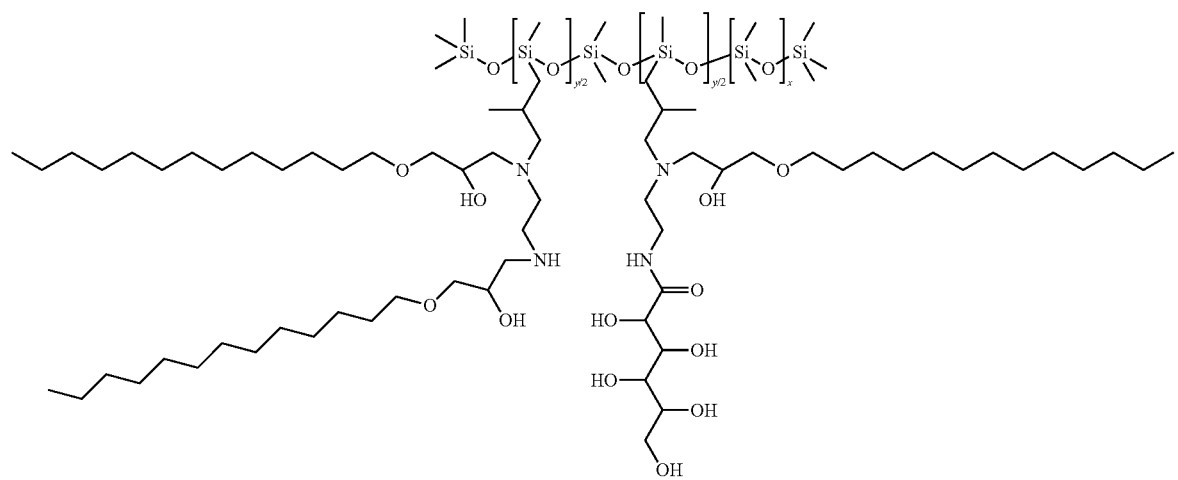

In the reaction scheme, subscript y was 8 to 10 and subscript x had a value sufficient to give the copolymer a DP of 350 to 400. Proton Nuclear Magnetic Resonance (H-NMR) was used to confirm the structure in the reaction scheme above.

Reference Example 2

H-NMR

H-NMR was used to confirm the completion of reaction. For each copolymer tested, 0.2 g of sample was weighed into a small vial, and 0.175 g of CD3OD (Aldrich) and 2.5-2.7 g of CDCl$_3$ containing 0.03% toluene were added to the vial containing the sample and mixed until miscible. Proton NMR spectra were generated using a Varian Mercury 300 MHz spectrometer. Functional group concentrations were obtained by peak integration of both the characteristic sample peaks and the toluene internal standard. The aldonamide proton on the carbon adjacent to the carbonyl was used to determine the aldonamide concentration by using an internal standard.

Reference Example 3

Short Chain Copolymer Synthesis

A copolymer was prepared as in Reference Example 1, except that a trimethylsiloxy terminated poly(dimethyl/methyl(aminoethylaminoisobutyl)siloxane), with a DP of 44 was used instead of the poly(dimethyl/methyl(aminoethylaminoisobutyl)siloxane) of Reference Example 1. In a 500 ml flask that was equipped with stirrer, reflux condenser, and temperature controller, 100 g of trimethylsiloxy terminated poly(dimethyl/methyl(aminoethylaminoisobutyl)siloxane), with a DP of 44 and an average 2.57 of aminoethylaminoisobutyl functional groups per molecule and 6.61 g of delta-gluconolactone were added. Then 106.6 g of Ethanol was added, and the mixture was reacted at 74° C. After four hours of reaction, 40.12 g of dodecyl/tetradecyl glycidyl ether was added and reacted for 8 hours. At the completion of the reaction ethanol was removed by stripping at 74° C. at full vacuum.

The reaction scheme of the second step was as follows.

H-NMR as described in Reference Example 2 was used to confirm the structure in the reaction scheme above.

Examples 1 and 2 and Comparative Example 1

The copolymers prepared in Reference Example 1 and Reference Example 3 were dispersed in various oils to determine compatibility. For comparative purposes a commercially available copolymer, ABIL® EM 90 a cetyl polyethylene glycol, polypropylene glycol functional polydimethylsiloxane from Evonik Goldschmidt Corporation of Hopewell, Va., U.S.A.

These emulsifiers were dispersed in the oils. In each sample, 9 grams of oil and 1 g of copolymer were mixed under ambient conditions. The results are in Table 1.

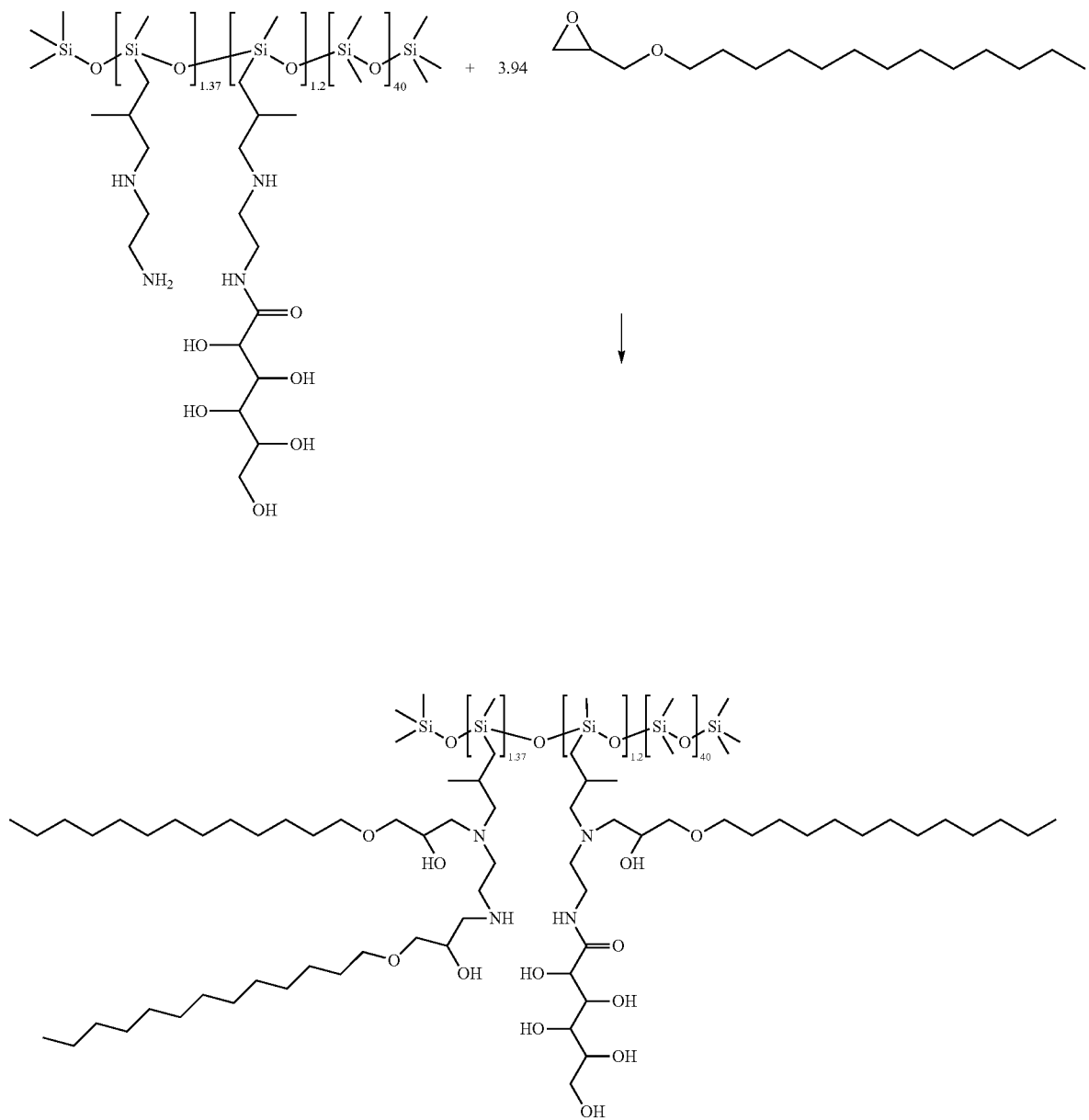

TABLE 1

Compatibility Test Results

| | Example | | Comparative |
|---|---|---|---|
| | 1 | 2 | Example 1 |
| | Copolymer | | |
| Oil | Copolymer of Reference Example 1B | Copolymer of Reference Example 3 | Abil 90 EM |
| 5 cSt 200 Fluid | clear | slightly hazy | hazy |
| FZ-3196 | clear | clear | clear |
| Isohexadecane | clear | clear | clear |
| Isopropyl Myristate | clear | clear | clear |
| Alkyl Benzoate | immiscible | slightly hazy | clear |
| Capric Triglyceride | immiscible | hazy | clear |
| Mineral Oil | immiscible | hazy | clear |

In Table 1, 5 cSt 200 Fluid refers to a polydimethylsiloxane having viscosity of 5 cSt available from Dow Corning Corporation as DOW CORNING® 200 Fluid, and FZ-3196 refers to a polydialkylsiloxane fluid available from Dow Corning Corporation.

Emulsion Examples 3-6 and Comparative Emulsion Examples 2-5

Oil phase samples were prepared by dispersing the copolymer of Reference Example 1 (shown as the product of the reaction scheme) and the copolymer of Reference Example 3 (shown as the product of the reaction scheme) in a silicone oil (5 cSt 200 Fluid, polydimethylsiloxane) and in an organic oil (isopropyl myristate). In each oil phase sample, 1 g of copolymer, 18 g of oil and 1 g absolute ethanol were mixed at ambient temperature overnight. For comparative purposes, the intermediates prepared in Reference Example 1 and Reference Example 3 (each shown as the first structure in the reaction schemes) were formulated into comparative oil phase samples. In each comparative oil phase sample, 1 g of intermediate, 18 g of oil and 1 g absolute ethanol were mixed at ambient temperature overnight. The results of the dispersion to prepare oil phase samples are shown in Table 1. The oil phase samples prepared using the copolymers of Reference Examples 1 and 3 formed clear solutions. The oil phase samples of the intermediates of Reference Examples 1 and 3 formed hazy mixtures when 5 cSt polydimethylsiloxane oil was used, and the oil phase samples of the intermediates of Reference Examples 1 and 3 did not mix when isopropyl myristate was used.

Samples of aqueous phase were prepared by adding 2 g NaCl to 78 g deionized water. The mixture was stirred until a clear solution was obtained.

Emulsion samples were prepared by adding 5 g increments of the aqueous phase to each of the 20 g oil phase samples. After each addition, the composition was mixed with a SpeedMixer from FlackTek at 3400 rpm for 50 seconds. A total of 80 g water phase was added to each oil phase sample using this procedure. The results are in Table 2.

TABLE 2

| | Example 3 | Example 4 | Example 5 | Example 6 | Comparative Example 2 | Comparative Example 3 | Comparative Example 4 | Comparative Example 5 |
|---|---|---|---|---|---|---|---|---|
| Emulsifier | Copolymer of RE 1B | Copolymer of RE 1A | Copolymer of RE 3 | Copolymer of RE3 | Intermediate of RE1B | Intermediate of RE1A | Intermediate of RE3 | Intermediate of RE3 |
| Average chain length of emusifier | 380 | 380 | 44 | 44 | 380 | 380 | 44 | 44 |
| Chain length/pendant group ratio of emusifier | 43.3 | 43.3 | 17.2 | 17.2 | 43.3 | 43.3 | 17.2 | 17.2 |
| C12/C14-Alkyl to Sugar ratio | 3 | 3 | 3 | 3 | 0 | 0 | 0 | 0 |
| Oil | 5 cSt 200 fl. | IPM | 5 cSt 200 fl. | IPM | 5 cSt 200 fl. | IPM | 5 cSt 200 fl. | IPM |
| Dispersion result | clear solution | clear solution | clear solution | clear solution | slightly hazy | not mixing | slightly hazy | not mixing |
| Emulsification result | w/o emulsion | w/o emulsion | w/o emulsion | w/o emulsion | w/o emulsion | no emulsion | w/o emulsion | no emulsion |

IPM refers to isopropyl myristate, and 5 cSt 200 fl. Refers to a polydimethylsiloxane having viscosity of 5 cSt available from Dow Corning Corporation as DOW CORNING® 200 Fluid. RE1A refers to Reference Example 1A. RE1B refers to Reference Example 1B. RE3 refers to Reference Example 3. W/O emulsion means that a water in oil emulsion formed.

Emulsification Procedure

Water in oil emulsion samples were prepared according to the following general procedure. The oil phase was prepared by mixing an emulsifier with an oil. The oil was isopropyl myristate or DOW CORNING® 200 Fluid, a silicone oil with a viscosity of 5 cSt, which is commercially available from Dow Corning Corporation. The emulsifier was a copolymer as described above or a comparative emulsifier. In each 20 gram (g) sample of oil phase, the oil phase contained 2 g emulsifier and 18 g oil.

The aqueous phase was prepared by mixing water and sodium chloride in a water:NaCl weight ratio ranging from 39:1 to 99:1. For each sample, 80 g of aqueous phase was prepared.

For each sample, the aqueous phase was added to the oil phase in 5 g increments. Between the addition of each increment, the sample was mixed for 40 seconds (s) at 3400 revolutions per minute (rpm) in a DAC150 FlackTek™ SpeedMixer™ (commercially available from FlackTek, Inc. of Landrum, S.C., U.S.A.) to provide a coarse emulsion.

After all the aqueous phase was added, the resulting coarse emulsion was subjected to shear at ≥7,000 rpm in a homogenizer (T25 Digital ULTRA-TURRAX® commercially available from IKA of Wilmington, N.C., U.S.A.) to provide the final emulsion sample.

Reference Example 4

Process for Making an Emulsion with Stirrer Mixer

Emulsions containing the ingredients in Tables 3, 5, and 7 using the copolymer as emulsifier were prepared by the following method:
1. The ingredients of phase A were mixed together to obtain a homogeneous mix.
2. The ingredients of phase B were mixed together to obtain a homogeneous mix
3. Phase B was added to phase A under mixing (with a cross stirrer). While adding phase B, mixing speed increased from 700 rpm to 1000 rpm.
4. After all phase B was added, the resulting product was mixed for 1 minute at 1000 rpm and 5 minutes at 2000 rpm. A coarse emulsion was obtained.
5. A 100 gram sample of the coarse emulsion was passed through a high shear mixing apparatus for 15 seconds to reduce the particle size. The high shear mixing apparatus was a lab mixer from Silverson Machines Ltd. of England. A fine emulsion was obtained.

Reference Example 5

Emulsion Stability

Stability of the emulsions 7-29 prepared herein was evaluated during storage of samples of each emulsion for 6 months at room temperature (RT), 40° C., and 50° C. Stability was measured by visual inspection. The results are in Tables 4, 6, and 8 below.

Reference Example 6

Freeze/Thaw Stability of Emulsions

Samples of the emulsions 7-29 prepared herein were evaluated for freeze/thaw stability. The procedure was as follows:
1. Emulsion samples were refrigerated at 4° C. for a minimum of 12 hours and then stored at RT for few hours.
2. Emulsion stability was evaluated. Stability was measured by visual inspection.
3. Steps 1 and 2 were repeated five times. The results are in Tables 4, 6, and 8 below.

TABLE 3

Emulsion Samples prepared with a stirrer mixer

| | | Sample Number | | | | | | |
|---|---|---|---|---|---|---|---|---|
| | Ingredient | 7 % | 8 % | 9 % | 10 % | 11 % | 12 % | 13 % |
| Phase A (oil) | Copolymer of Reference Example 3 | 1 | 1 | 2 | 2 | 2 | 1 | 1 |
| | Xiameter ® PMX-200 Silicone Fluid 5CS | / | / | / | / | 18 | / | / |
| | Xiameter ® PMX-Silicone 200 Fluid 5CS/Crodamol GTCC (50%/50% mixture) | 19 | / | 18 | / | / | 9 | 39 |
| | Mineral Oil | / | 19 | / | 18 | / | / | / |
| Phase B (aqueous) | Water | 74 | 74 | 74 | 74 | 74 | 84 | 54 |
| | Glycerin | 5 | 5 | 5 | 5 | 5 | 5 | 5 |
| | NaCl | 1 | 1 | 1 | 1 | 1 | 1 | 1 |

In the tables, Crodamol GTCC refers to a medium chain triglyceride of low viscosity, which is used as an emollient. Crodamol GTCC is commercially available from Croda, Inc. of Edison, New jersey, U.S.A.

TABLE 4

Results of Evaluation of Emulsions in Table 3

Viscosity (Brookfield DV-II-Spindle 6, 2.5 rpm)

| 1 day | 38400 | / | 50800 | 151000 | 115000 | / | 3200 |
|---|---|---|---|---|---|---|---|
| 1 week | 46000 | / | 71000 | 133000 | 104000 | / | 3200 |
| 2 weeks | 32000 | / | 74800 | 108000 | 106000 | / | 3200 |
| 3 weeks | 15200 | / | 74400 | 104000 | 98700 | / | 2800 |
| 1 month | 16400 | / | 72800 | 108000 | 85200 | / | 2800 |
| 2 months | / | / | 74800 | 84800 | / | / | / |
| 3 months | / | / | 69200 | 82000 | / | / | / |
| 4 months | / | / | 66800 | 75600 | / | / | / |

TABLE 4-continued

Results of Evaluation of Emulsions in Table 3

Stability

| | | | | | | | |
|---|---|---|---|---|---|---|---|
| At RT | stable at least 3 months | almost broken after high shear mixing- Broken after 1 day | stable at least 4 months | stable at least 4 months | stable for 2 months | broken after high shear mixing | stable for 4 weeks |
| At 40° C. | stable for 2 months | / | stable at least 4 months | stable for 4 weeks | stable for 4 weeks | / | / |
| At 50° C. | stable for 3 weeks | / | stable for 3 weeks | stable at least 4 months | stable for 3 weeks | / | stable for 2 weeks |
| F/T Cycle | 0 | / | 0 | 0 | 0 | / | at least 4 cycles |
| Sample | 7 | 8 | 9 | 10 | 11 | 12 | 13 |

TABLE 5

Emulsion Samples prepared with a stirrer mixer

| | | Sample Number | | | | | | | |
|---|---|---|---|---|---|---|---|---|---|
| | Ingredient | 14 % | 15 % | 16 % | 17 % | 18 % | 19 % | 20 % | 21 % |
| Phase A | Copolymer of Reference Example 1A | 4 | 4 | 8 | 8 | 8 | 4 | 4 | 8 |
| | Xiameter ® PMX-200 Silicone Fluid 5 cSt | / | / | / | / | 12 | / | / | / |
| | Xiameter ® PMX-Silicone 200 Fluid 5 cSt Crodamol GTCC (50%/50% mixture) | 16 | / | 12 | / | / | 6 | 36 | 32 |
| | Mineral Oil | / | 16 | / | 12 | / | / | / | / |
| Phase B | Water | 74 | 74 | 74 | 74 | 74 | 84 | 54 | 54 |
| | Glycerin | 5 | 5 | 5 | 5 | 5 | 5 | 5 | 5 |
| | NaCl | 1 | 1 | 1 | 1 | 1 | 1 | 1 | 1 |

TABLE 6

Results of Evaluation of Emulsions in Table 5

Viscosity (Brookfield DV-II-Spindle 6, 2.5 rpm) (cP)

| | | | | | | | | |
|---|---|---|---|---|---|---|---|---|
| 1 day | 190000 | 148000 | 74400 | 112000 | 214000 | / | 14000 | 16200 |
| 1 week | 184000 | 80000 | 78400 | 78000 | 188000 | / | 10400 | 14700 |
| 2 weeks | 204000 | 83000 | 81200 | 61000 | 187000 | / | / | / |
| 3 weeks | / | / | 82800 | 57000 | 179000 | / | / | / |
| 1 month | 213000 | 133000 | 81000 | 45200 | 183000 | / | / | / |
| 2 months | / | / | 84400 | 44400 | 187000 | / | / | / |
| 3 months | / | / | 80400 | 38000 | 180000 | / | / | / |
| 4 months | / | / | 72000 | / | 166000 | / | / | / |

Stability

| | | | | | | | | |
|---|---|---|---|---|---|---|---|---|
| At RT | stable at least 3 months | stable at least 3 months | stable at least 4 months | stable for 3 months | stable at least 4 months | Broken during the process | stable for 1 week | stable for 1 week |
| At 40° C. | stable for 2 months | stable at least 3 months | stable at least 4 months | stable for 3 weeks | stable at least 4 months | / | stable for 1 week | stable for 1 week |
| At 50° C. | stable for 3 months | stable at least 3 months | stable for 4 weeks | stable for 3 months | stable at least 4 months | / | stable for 1 week | stable for 1 week |
| F/T Cycle | 1 cycle | 0 | 0 | 0 | 5 cycles | / | 0 | 0 |
| Sample | 14 | 15 | 16 | 17 | 18 | 19 | 20 | 21 |

TABLE 7

Emulsion Samples prepared with a stirrer mixer

| | | Sample Number | | | | | | | |
|---|---|---|---|---|---|---|---|---|---|
| | Ingredient | 22 % | 23 % | 24 % | 25 % | 26 % | 27 % | 28 % | 29 % |
| Phase A | Copolymer of Reference Example 1B | 4 | 4 | 8 | 8 | 8 | 4 | 4 | 8 |
| | Xiameter® PMX-200 Silicone Fluid 5 cSt | / | / | / | / | 12 | / | / | / |
| | Xiameter® PMX-Silicone 200 Fluid 5 cSt/ Crodamol GTCC (50%/50%) | 16 | / | 12 | / | / | 6 | 36 | 32 |
| | Mineral Oil | / | 16 | / | 12 | / | / | / | / |
| Phase B | Water | 74 | 74 | 74 | 74 | 74 | 84 | 54 | 54 |
| | Glycerin | 5 | 5 | 5 | 5 | 5 | 5 | 5 | 5 |
| | NaCl | 1 | 1 | 1 | 1 | 1 | 1 | 1 | 1 |

TABLE 8

Results of Evaluation of Emulsions in Table 7

| Viscosity (Brookfield DV-II-Spindle 6, 2.5 rpm) (cP) | | | | | | | | |
|---|---|---|---|---|---|---|---|---|
| 1 day | 105000 | / | 236000 | 195000 | 143000 | / | 9200 | 16600 |
| 1 week | 106000 | / | 234000 | 136000 | 127000 | / | 5600 | 15500 |
| 2 weeks | 102000 | / | 206000 | 95600 | 130000 | / | / | / |
| 3 weeks | / | / | 20400 | 82700 | 131000 | / | / | / |
| 1 month | / | / | 20500 | 84800 | 120000 | / | / | / |
| 2 months | / | / | 195000 | 84000 | 120000 | / | / | / |
| 3 months | / | / | 185000 | 78800 | 112000 | / | / | / |
| 4 months | / | / | 147000 | 75200 | | / | / | / |
| Stability | | | | | | | | |
| At RT | stable at least 3 months | broken after high shear mixing | stable at least 4 months | stable at least 4 months | stable at least 3 months | Impossible to emulsify | stable for 1 week | stable for 1 week |
| At 40° C. | stable for 2 months | / | stable for 2 months | stable at least 4 months | stable at least 3 months | / | stable for 1 week | stable for 1 week |
| At 50° C. | stable for 1 month | / | / | stable at least 4 months | stable for 1 month | / | stable for 1 week | stable for 1 week |
| F/T Cycle | 1 cycle | / | 5 | 0 | 1 | / | 0 | 0 |
| Sample | 22 | 23 | 24 | 25 | 26 | 27 | 28 | 29 |

INDUSTRIAL APPLICABILITY

The copolymer described above is useful as an emulsifier for water in oil (w/o) type emulsions, particularly where the oil comprises a silicone and/or an organic oil. The copolymer may provide an emulsion with low odor, i.e., lower odor than as compared to emulsions containing silicone polyether emulsifiers. The copolymer may also provide an emulsion which is nonirritating to the skin, i.e., the a personal care product containing a safe and effective amount of the emulsion containing the copolymer is suitable for application to skin.

The invention claimed is:

1. A method of making a copolymer of formula:

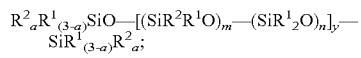

where
each $R^1$ can be the same or different and each $R^1$ comprises hydrogen, an alkyl group, an organic group, or a group of formula $R^3$-Q;

Q comprises an epoxy, cycloalkylepoxy, primary or secondary amino, ethylenediamine, carboxy, halogen, vinyl, allyl, anhydride, or mercapto functionality;

subscripts m and n are integers from 0 to 10,000 and may be the same or different;

each subscript a is independently 0, 1, 2, or 3; subscript y is an integer such that the copolymer has a molecular weight less than 1 million;

each $R^2$ has formula $Z$-$(G^1)_b$-$(G^2)_c$, and there is an average of at least one $R^2$ per copolymer molecule, where $G^1$ is a saccharide component comprising 5 to 12 carbon atoms, a quantity (b+c) has a value ranging from 1 to 10, and subscript b or subscript c can be 0, $G^2$ is a saccharide component comprising 5 to 12 carbon atoms additionally substituted with organic or organosilicon radicals, each Z is a linking group and is independently selected from the group consisting of: —$R^3$—N($R^8$)—C(O)—$R^4$—, —$R^3$—CH(OH)—CH$_2$—N($R^8$)—$R^4$—, or —$R^3$—CH(N($R^4$)($R^8$))CH$_2$OH;

where each $R^3$ and each $R^4$ are divalent spacer groups comprising a group of formula $(R^5)_r(R^6)_s(R^7)_t$, where at least one of subscripts r, s and t is 1, and each $R^5$ and each $R^7$ are independently either an alkylene group of 1 to 12 carbon atoms or a group of formula $(R^9O)_p$, where subscript p is an integer with a value ranging from 1 to 50, and each $R^9$ is a divalent organic group, and each $R^9O$ may be the same or different, each $R^6$ is —N($R^8$)—, where $R^8$ is selected from $R^3$, a monovalent hydrocarbon group, or a reaction product of —N(H)— with an epoxy functional group, a cycloalylepoxy functional group, a glycidyl ether functional group, an acid anhydride functional group, or a lactone; each X is independently a divalent a carboxylic acid, phosphate, sulfate, sulfonate or quaternary ammonium radical, and with the proviso that each $R^3$ and each $R^4$ may be the same or different;

where the method comprises the steps of:
i) reacting an organofunctional polyorganosiloxane with a sugar moiety to produce the saccharide siloxane copolymer in the presence of a solvent;
optionally ii) removing a portion of the solvent; and
iii) adding an oil, where step i) is performed by reacting ingredients comprising:
(A) an epoxy-functional polyorganosiloxane, and
(B) an n-alkyl glucamine.

2. The method of claim 1, where ingredient (A) is $$R^{15}_x\!-\!\underset{\underset{R^{12}_{(3-x)}}{|}}{\overset{\overset{R^{12}}{|}}{Si}}\!-\!O\!-\!\left(\underset{\underset{R^{12}}{|}}{\overset{\overset{R^{12}}{|}}{Si}}\!-\!O\right)_{\!v}\!\left(\underset{\underset{R^{15}_x}{|}}{\overset{\overset{R^{12}}{|}}{Si}}\!-\!O\right)_{\!w}\!\underset{\underset{R^{12}_{(3-x)}}{|}}{\overset{\overset{R^{12}_{(3-x)}}{|}}{Si}}\!-\!R^{15}_x,$$

where
each $R^{12}$ is independently a monovalent hydrocarbon group;
each $R^{15}$ is independently an epoxy functional organic group;
each subscript x is independently 0 or 1;
subscript v has a value ranging from 0 to 10,000; and
subscript w has a value ranging from 0 to 10,000.

3. The method of claim 1, where the n-alkyl glucamine is n-methyl glucamine.

4. The method of claim 1, further comprising preparing the epoxy functional polyorganosiloxane by hydrosilylation of ingredients comprising an alkenyl functional epoxy containing compound and a polyorganohydrogensiloxane.

5. The method of claim 4, where the alkenyl functional epoxy containing compound is allyl glycidyl ether, dodecyl glycidyl ether, tetradecyl glycidyl ether, or octadecylglycidyl ether.

6. The method of claim 1, where the ingredients further comprise an alkene.

7. The method of claim 6, where the alkene comprises undecene.

8. The method of claim 1, where step i) is performed by a method comprising:
1) reacting (a) an n-alkyl-glucamine with (b) an alkenyl functional epoxy compound, and
2) hydrosilylating the product of step 1) with (c) a polyorganohydrogensiloxane.

9. The method of claim 8, where the n-alkyl glucamine is n-methyl glucamine.

10. The method of claim 8, where the alkenyl functional epoxy containing compound is allyl glycidyl ether, dodecyl glycidyl ether, tetradecyl glycidyl ether, or octadecylglycidyl ether.

11. The method of claim 1, where the product of step i) contains secondary amine functionality, further comprising a step of reacting the product of step i) with a capping agent selected from a lactone, a halogenated unsaturated compound, an epoxy functional compound, or an acid anhydride.

12. The method of claim 1, where the solvent is an alcohol selected from methanol, ethanol, n-propanol, isopropanol, 2-propanol, isobutanol, n-butanol, and combinations thereof.

13. The method of claim 1, where the oil is a silicone oil.

14. The method of claim 13, where the oil is a polydialkylsiloxane.

15. The method of claim 1, where the oil is an organic oil selected from a hydrocarbon oil, an ester, a vegetable oil, a mineral oil, or a fatty alcohol.

16. A method for preparing an emulsion comprising
I) adding an aqueous phase to the product prepared by the method of claim 1, and
II) mixing.

17. The method of claim 16, where the method further comprises step III) subjecting the emulsion to shear during and/or after step II).

18. The method of claim 16, where step I) and step II) are performed incrementally by adding a portion of the aqueous phase, mixing, and thereafter repeating until all of the aqueous phase is added.

19. The method of claim 16, where step I) and step II) are performed by adding the aqueous phase continuously over a period of time while mixing is performed.

20. The method of claim 16, where the aqueous phase is present in an amount ranging from 20% to 95% by weight based on the weight of the emulsion.

21. An emulsion comprising:
A) an aqueous phase,
B) an oil phase having an oil, and
C) an emulsifier, where the emulsifier is a saccharide siloxane copolymer prepared by the method of claim 7, where the copolymer and the oil are present in an amounts such that a weight ratio of copolymer/oil ranges from 1/1 to 1/50.

22. The emulsion of claim 21, where the aqueous phase is discontinuous and the oil phase is continuous.

23. The emulsion of claim 21 where the oil phase comprises a silicone oil.

24. The emulsion of claim 23, where the silicone oil is a polydialkylsiloxane.

25. The emulsion of claim 21 where the oil is an organic oil selected from a hydrocarbon oil, an ester, a vegetable oil, a mineral oil, or a fatty alcohol.

26. A composition comprising:
(A) the emulsion according to claim 21, and
(B) an additional ingredient.

27. The composition of claim 26, where ingredient (B) is selected from: additional silicones, aerosols, anti-oxidants, cleansing agents, colorants, additional conditioning agents, deposition agents, electrolytes, emollients and oils, exfoliating agents, foam boosters, fragrances, humectants, occlusive agents, pediculicides, pH control agents, pigments, preservatives, biocides, other solvents, stabilizers, sunscreening agents, suspending agents, tanning agents, other surfactants, thickeners, vitamins, botanicals, waxes, rheology-modifying agents, antiperspirants, anti-dandruff, anti-acne, anti-carie and wound healing-promotion agents, an additional oil, a hydrophilic medium, a filler, a fiber, a film forming polymer, an additional surfactant and/or emulsifier, a dyestuff, a structuring agent, an active ingredient, a fragrance, a preservative, and combinations thereof.

28. A composition according to claim 26, where the composition is a personal care composition adapted to provide a benefit to a portion of the body to which it is applied.

29. The composition of claim 28, where the personal care composition is selected from antiperspirants and deodorants, skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, wrinkle fillers, skin imperfection hiders, skin surface smoothers, eyelash curlers, nail varnishes, hair make-up products, eye shadows, body makeups, and powders, medicament creams, pastes or sprays including anti-acne, dental hygienic, antibiotic, healing promotive, nutritive, which may be preventative and/or therapeutic.

30. A method of making the emulsion of claim 21, comprising:
   1) dispersing the copolymer in the oil,
   2) adding the aqueous phase to the product of step 1), and
   3) mixing.

31. The method of claim 30, where the method further comprises subjecting the emulsion to shear during and/or after step 2).

32. The method of claim 30, where step 2) and step 3) are performed incrementally by adding a portion of the aqueous phase, mixing, and thereafter repeating until all of the aqueous phase is added.

* * * * *